(12) United States Patent
Whitman et al.

(10) Patent No.: US 8,740,932 B2
(45) Date of Patent: Jun. 3, 2014

(54) SURGICAL DEVICE

(71) Applicant: Covidien LP, Mansfield, MA (US)

(72) Inventors: Michael P. Whitman, New Hope, PA (US); John E. Burbank, Ridgefield, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/964,228

(22) Filed: Aug. 12, 2013

(65) Prior Publication Data

US 2014/0021238 A1     Jan. 23, 2014

Related U.S. Application Data

(60) Continuation of application No. 13/207,697, filed on Aug. 11, 2011, now Pat. No. 8,512,359, which is a continuation of application No. 12/749,573, filed on Mar. 3, 2010, now Pat. No. 8,021,373, which is a division of application No. 09/999,546, filed on Nov. 30, 2001, now Pat. No. 7,695,485.

(51) Int. Cl.
*A61B 17/068*     (2006.01)

(52) U.S. Cl.
USPC ............................ 606/205; 606/143; 606/167

(58) Field of Classification Search
USPC ............ 606/143, 205–207; 227/175.1–182.1
See application file for complete search history.

(56) References Cited

U.S. PATENT DOCUMENTS

| | | | |
|---|---|---|---|
| 1,798,902 A | 3/1931 | Raney | |
| 1,881,250 A | 10/1932 | Tomlinson | |
| 2,031,682 A | 2/1936 | Wappler et al. | |
| 2,174,219 A | 9/1939 | Balma | |
| 2,246,647 A | 6/1941 | Vancura | |
| 2,419,045 A | 4/1947 | Whittaker | |
| 2,725,628 A | 12/1955 | O'Neilly et al. | |
| 3,006,344 A | 10/1961 | Vogelfanger | |
| 3,079,606 A | 3/1963 | Bobrov et al. | |
| 3,120,845 A | 2/1964 | Homer | |
| 3,193,165 A | 7/1965 | Akhalaya et al. | |
| 3,252,643 A | 5/1966 | Strekopov et al. | |
| 3,256,875 A | 6/1966 | Tsepelev et al. | |
| 3,275,211 A | 9/1966 | Hirsch et al. | |
| 3,315,863 A | 4/1967 | O'Dea | |

(Continued)

FOREIGN PATENT DOCUMENTS

| DE | 2044108 A1 | 3/1972 |
|---|---|---|
| DE | 2330182 A1 | 1/1975 |

(Continued)

OTHER PUBLICATIONS

European Search Report for corresponding EP10012644, dated Mar. 3, 2011.

*Primary Examiner* — Ryan Severson

(57) ABSTRACT

A surgical device includes a first jaw and a second jaw disposed in opposed correspondence with the first jaw. The second jaw is mechanically coupled to the first jaw at a proximal end opposite a distal end. A cutting element is disposed within the second jaw, and a first driver is configured to move the cutting element proximally from the distal end toward the proximal end of the second jaw to cut a section of tissue disposed between the first and second jaws. The device may also include a stapling element disposed within the second jaw. The cutting element and the stapling element may be contiguous so as to define a cutting and stapling element, such as a wedge having a blade disposed thereon.

20 Claims, 23 Drawing Sheets

(56) References Cited

U.S. PATENT DOCUMENTS

| | | |
|---|---|---|
| 3,317,105 A | 5/1967 | Astafjev et al. |
| 3,388,847 A | 6/1968 | Kasulin et al. |
| 3,490,675 A | 1/1970 | Green et al. |
| 3,494,533 A | 2/1970 | Green et al. |
| 3,499,591 A | 3/1970 | Green |
| 3,552,626 A | 1/1971 | Astafiev et al. |
| 3,568,659 A | 3/1971 | Karnegis |
| 3,589,589 A | 6/1971 | Akopov |
| 3,593,903 A | 7/1971 | Astafiev et al. |
| 3,618,842 A | 11/1971 | Bryan |
| 3,638,652 A | 2/1972 | Kelley |
| 3,643,851 A | 2/1972 | Green et al. |
| 3,662,939 A | 5/1972 | Bryan |
| 3,675,688 A | 7/1972 | Bryan et al. |
| 3,692,224 A | 9/1972 | Astafiev et al. |
| 3,717,294 A | 2/1973 | Green |
| 3,735,762 A | 5/1973 | Bryan et al. |
| 3,777,538 A | 12/1973 | Weatherly et al. |
| 3,788,303 A | 1/1974 | Hall |
| 3,795,034 A | 3/1974 | Strekopytov et al. |
| 3,815,476 A | 6/1974 | Green et al. |
| 3,819,100 A | 6/1974 | Noiles et al. |
| 3,837,555 A | 9/1974 | Green |
| 3,844,289 A | 10/1974 | Noiles |
| 3,858,577 A | 1/1975 | Bass et al. |
| 3,859,986 A | 1/1975 | Okada et al. |
| 3,882,854 A | 5/1975 | Hulka et al. |
| 3,892,228 A | 7/1975 | Mitsui |
| 3,935,981 A | 2/1976 | Akopov et al. |
| 3,949,924 A | 4/1976 | Green |
| 3,952,748 A | 4/1976 | Kaliher et al. |
| RE28,932 E | 8/1976 | Noiles et al. |
| 4,014,492 A | 3/1977 | Rothfuss |
| 4,027,510 A | 6/1977 | Hiltebrandt |
| 4,060,089 A | 11/1977 | Noiles |
| 4,064,881 A | 12/1977 | Meredith |
| 4,071,029 A | 1/1978 | Richmond et al. |
| 4,085,756 A | 4/1978 | Weaver |
| 4,086,926 A | 5/1978 | Green et al. |
| 4,092,986 A | 6/1978 | Schneiderman |
| 4,111,206 A | 9/1978 | Vishnevsky et al. |
| 4,169,476 A | 10/1979 | Hiltebrandt |
| 4,198,960 A | 4/1980 | Utsugi |
| 4,198,982 A | 4/1980 | Fortner et al. |
| 4,202,479 A | 5/1980 | Razgulov et al. |
| 4,202,480 A | 5/1980 | Annett |
| 4,207,873 A | 6/1980 | Kruy |
| 4,207,898 A | 6/1980 | Becht |
| 4,244,372 A | 1/1981 | Kapitanov et al. |
| 4,261,244 A | 4/1981 | Becht et al. |
| 4,273,111 A | 6/1981 | Tsukaya |
| 4,273,129 A | 6/1981 | Boebel |
| 4,286,585 A | 9/1981 | Ogawa |
| 4,289,131 A | 9/1981 | Mueller |
| 4,289,133 A | 9/1981 | Rothfuss |
| 4,296,881 A | 10/1981 | Lee |
| 4,304,236 A | 12/1981 | Conta et al. |
| 4,310,115 A | 1/1982 | Inoue |
| 4,319,576 A | 3/1982 | Rothfuss |
| 4,325,377 A | 4/1982 | Boebel |
| 4,334,539 A | 6/1982 | Childs et al. |
| 4,349,028 A | 9/1982 | Green |
| 4,351,466 A | 9/1982 | Noiles |
| 4,354,628 A | 10/1982 | Green |
| 4,367,729 A | 1/1983 | Ogiu |
| 4,379,457 A | 4/1983 | Gravener et al. |
| 4,383,634 A | 5/1983 | Green |
| 4,391,401 A | 7/1983 | Moshofsky |
| 4,402,311 A | 9/1983 | Hattori |
| 4,402,445 A | 9/1983 | Green |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,461,305 A | 7/1984 | Cibley |
| 4,473,077 A | 9/1984 | Noiles et al. |
| 4,476,863 A | 10/1984 | Kanshin et al. |
| 4,485,811 A | 12/1984 | Chernousov et al. |
| 4,485,817 A | 12/1984 | Swiggett |
| 4,487,270 A | 12/1984 | Huber |
| 4,488,523 A | 12/1984 | Shichman |
| 4,489,724 A | 12/1984 | Arnegger |
| 4,489,875 A | 12/1984 | Crawford et al. |
| 4,494,057 A | 1/1985 | Hotta |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,506,670 A | 3/1985 | Crossley |
| 4,506,671 A | 3/1985 | Green |
| 4,513,746 A | 4/1985 | Aranyi et al. |
| 4,519,532 A | 5/1985 | Foslien |
| 4,520,817 A | 6/1985 | Green |
| 4,527,724 A | 7/1985 | Chow et al. |
| 4,534,352 A | 8/1985 | Korthoff |
| 4,534,420 A | 8/1985 | Goldelius |
| 4,535,773 A | 8/1985 | Yoon |
| 4,559,928 A | 12/1985 | Takayama |
| 4,566,620 A | 1/1986 | Green et al. |
| 4,573,468 A | 3/1986 | Conta et al. |
| 4,573,622 A | 3/1986 | Green et al. |
| 4,574,806 A | 3/1986 | McCarthy |
| 4,576,167 A | 3/1986 | Noiles |
| 4,589,412 A | 5/1986 | Kensey |
| 4,589,416 A | 5/1986 | Green |
| 4,589,582 A | 5/1986 | Bilotti |
| 4,591,085 A | 5/1986 | Di Giovanni |
| 4,592,354 A | 6/1986 | Rothfuss |
| 4,593,679 A | 6/1986 | Collins |
| 4,603,693 A | 8/1986 | Conta et al. |
| 4,605,001 A | 8/1986 | Rothfuss et al. |
| 4,606,343 A | 8/1986 | Conta et al. |
| 4,607,638 A | 8/1986 | Crainich |
| 4,608,981 A | 9/1986 | Rothfuss et al. |
| 4,610,383 A | 9/1986 | Rothfuss et al. |
| D286,567 S | 11/1986 | Lichtman et al. |
| 4,631,052 A | 12/1986 | Kensey |
| 4,633,861 A | 1/1987 | Chow et al. |
| 4,633,874 A | 1/1987 | Chow et al. |
| 4,643,190 A | 2/1987 | Heimberger |
| 4,644,952 A | 2/1987 | Patipa et al. |
| 4,646,745 A | 3/1987 | Noiles |
| 4,655,673 A | 4/1987 | Hawkes |
| 4,657,017 A | 4/1987 | Sorochenko |
| 4,664,305 A | 5/1987 | Blake, III et al. |
| 4,667,673 A | 5/1987 | Li |
| 4,669,471 A | 6/1987 | Hayashi |
| 4,671,445 A | 6/1987 | Barker et al. |
| 4,672,961 A | 6/1987 | Davies |
| 4,674,515 A | 6/1987 | Andou et al. |
| 4,688,555 A | 8/1987 | Wardle |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,714,187 A | 12/1987 | Green |
| 4,728,020 A | 3/1988 | Green et al. |
| 4,732,156 A | 3/1988 | Nakamura |
| 4,733,118 A | 3/1988 | Mihalko |
| 4,742,815 A | 5/1988 | Ninan et al. |
| 4,752,024 A | 6/1988 | Green et al. |
| 4,754,909 A | 7/1988 | Barker et al. |
| 4,756,309 A | 7/1988 | Sachse et al. |
| 4,760,840 A | 8/1988 | Fournier, Jr. et al. |
| 4,763,669 A | 8/1988 | Jaeger |
| 4,767,044 A | 8/1988 | Green |
| 4,771,774 A | 9/1988 | Simpson et al. |
| 4,776,506 A | 10/1988 | Green |
| 4,781,186 A | 11/1988 | Simpson et al. |
| 4,784,137 A | 11/1988 | Kulik et al. |
| 4,789,090 A | 12/1988 | Blake, III |
| 4,796,793 A | 1/1989 | Smith et al. |

(56) References Cited

U.S. PATENT DOCUMENTS

| | | | |
|---|---|---|---|
| 4,805,823 | A | 2/1989 | Rothfuss |
| 4,815,469 | A | 3/1989 | Cohen et al. |
| 4,817,847 | A | 4/1989 | Redtenbacher et al. |
| 4,819,632 | A | 4/1989 | Davies |
| 4,819,853 | A | 4/1989 | Green |
| 4,841,888 | A | 6/1989 | Mills et al. |
| 4,848,637 | A | 7/1989 | Pruitt |
| 4,858,608 | A | 8/1989 | McQuilkin |
| 4,863,088 | A | 9/1989 | Redmond et al. |
| 4,867,158 | A | 9/1989 | Sugg |
| 4,869,415 | A | 9/1989 | Fox |
| 4,873,977 | A | 10/1989 | Avant et al. |
| 4,887,599 | A | 12/1989 | Muller |
| 4,887,612 | A | 12/1989 | Esser et al. |
| 4,890,602 | A | 1/1990 | Hake |
| 4,892,244 | A | 1/1990 | Fox et al. |
| 4,893,613 | A | 1/1990 | Hake |
| 4,893,622 | A | 1/1990 | Green et al. |
| 4,903,697 | A | 2/1990 | Resnick et al. |
| 4,907,591 | A | 3/1990 | Vasconcellos et al. |
| 4,917,114 | A | 4/1990 | Green et al. |
| 4,919,152 | A | 4/1990 | Ger |
| 4,928,699 | A | 5/1990 | Sasai |
| 4,930,494 | A | 6/1990 | Takehana et al. |
| 4,932,960 | A | 6/1990 | Green et al. |
| 4,936,845 | A | 6/1990 | Stevens |
| 4,941,454 | A | 7/1990 | Wood et al. |
| 4,941,623 | A | 7/1990 | Pruitt |
| 4,944,093 | A | 7/1990 | Falk |
| 4,944,443 | A | 7/1990 | Oddsen et al. |
| 4,955,882 | A | 9/1990 | Hakky |
| 4,955,959 | A | 9/1990 | Tompkins et al. |
| 4,957,499 | A | 9/1990 | Lipatov et al. |
| 4,962,877 | A | 10/1990 | Hervas |
| 4,976,688 | A | 12/1990 | Rosenblum |
| 4,976,710 | A | 12/1990 | Mackin |
| 4,977,900 | A | 12/1990 | Fehling et al. |
| 4,978,049 | A | 12/1990 | Green |
| 4,982,726 | A | 1/1991 | Taira |
| 4,991,764 | A | 2/1991 | Mericle |
| 4,994,060 | A | 2/1991 | Rink et al. |
| 4,995,877 | A | 2/1991 | Ams et al. |
| 5,005,749 | A | 4/1991 | Aranyi |
| 5,018,657 | A | 5/1991 | Pedlick et al. |
| 5,031,814 | A | 7/1991 | Tompkins et al. |
| 5,040,715 | A | 8/1991 | Green et al. |
| 5,059,203 | A | 10/1991 | Husted |
| 5,065,929 | A | 11/1991 | Schulze et al. |
| D322,143 | S | 12/1991 | Spreckelmeier |
| 5,071,430 | A | 12/1991 | de Salis et al. |
| 5,077,506 | A | 12/1991 | Krause |
| 5,100,041 | A | 3/1992 | Storace |
| 5,104,025 | A | 4/1992 | Main et al. |
| 5,108,391 | A | 4/1992 | Flachenecker et al. |
| 5,114,065 | A | 5/1992 | Storace |
| 5,119,983 | A | 6/1992 | Green et al. |
| 5,129,570 | A | 7/1992 | Schulze et al. |
| 5,133,359 | A | 7/1992 | Kedem |
| 5,133,713 | A | 7/1992 | Huang et al. |
| 5,139,513 | A | 8/1992 | Segato |
| 5,156,315 | A | 10/1992 | Green et al. |
| 5,157,837 | A | 10/1992 | Rose |
| 5,158,222 | A | 10/1992 | Green et al. |
| 5,170,925 | A | 12/1992 | Madden et al. |
| 5,171,247 | A | 12/1992 | Hughett et al. |
| 5,171,251 | A | 12/1992 | Bregen et al. |
| 5,173,133 | A | 12/1992 | Morin et al. |
| 5,192,292 | A | 3/1993 | Cezana et al. |
| 5,197,649 | A | 3/1993 | Bessler et al. |
| 5,201,325 | A | 4/1993 | McEwen et al. |
| 5,201,750 | A | 4/1993 | Hocherl et al. |
| 5,205,459 | A | 4/1993 | Brinkerhoff et al. |
| 5,207,691 | A | 5/1993 | Nardella |
| 5,207,697 | A | 5/1993 | Carusillo et al. |
| 5,217,003 | A | 6/1993 | Wilk |
| 5,217,460 | A | 6/1993 | Knoepfler |
| 5,221,279 | A | 6/1993 | Cook et al. |
| 5,224,951 | A | 7/1993 | Freitas |
| 5,226,426 | A | 7/1993 | Yoon |
| 5,237,884 | A | 8/1993 | Seto |
| 5,243,967 | A | 9/1993 | Hibino |
| 5,249,583 | A | 10/1993 | Mallaby |
| 5,253,793 | A | 10/1993 | Green et al. |
| 5,254,117 | A | 10/1993 | Rigby et al. |
| 5,258,004 | A | 11/1993 | Bales et al. |
| 5,258,007 | A | 11/1993 | Spetzler et al. |
| 5,258,008 | A | 11/1993 | Wilk |
| 5,261,877 | A | 11/1993 | Fine et al. |
| 5,267,997 | A | 12/1993 | Farin et al. |
| 5,268,622 | A | 12/1993 | Philipp |
| 5,271,543 | A | 12/1993 | Grant et al. |
| 5,271,544 | A | 12/1993 | Fox et al. |
| RE34,519 | E | 1/1994 | Fox et al. |
| 5,275,322 | A | 1/1994 | Brinkerhoff et al. |
| 5,275,323 | A | 1/1994 | Schulze et al. |
| 5,275,609 | A | 1/1994 | Pingleton et al. |
| 5,279,565 | A | 1/1994 | Klein et al. |
| 5,285,945 | A | 2/1994 | Brinkerhoff et al. |
| 5,289,963 | A | 3/1994 | McGarry et al. |
| 5,290,299 | A | 3/1994 | Fain et al. |
| 5,290,303 | A | 3/1994 | Pingleton et al. |
| 5,292,053 | A | 3/1994 | Bilotti et al. |
| 5,295,990 | A | 3/1994 | Levin |
| 5,300,087 | A | 4/1994 | Knoepfler |
| 5,307,976 | A | 5/1994 | Olson et al. |
| 5,312,023 | A | 5/1994 | Green et al. |
| 5,312,434 | A | 5/1994 | Crainich |
| 5,314,436 | A | 5/1994 | Wilk |
| 5,318,221 | A | 6/1994 | Green et al. |
| 5,320,627 | A | 6/1994 | Sorensen et al. |
| 5,322,055 | A | 6/1994 | Davison et al. |
| 5,324,288 | A | 6/1994 | Billings et al. |
| 5,324,300 | A | 6/1994 | Elias et al. |
| 5,326,013 | A | 7/1994 | Green et al. |
| 5,330,471 | A | 7/1994 | Eggers |
| 5,330,486 | A | 7/1994 | Wilk |
| 5,333,772 | A | 8/1994 | Rothfuss et al. |
| 5,333,773 | A | 8/1994 | Main et al. |
| 5,336,229 | A | 8/1994 | Noda |
| 5,342,299 | A | 8/1994 | Snoke et al. |
| 5,342,381 | A | 8/1994 | Tidemand |
| 5,342,382 | A | 8/1994 | Brinkerhoff et al. |
| 5,344,420 | A | 9/1994 | Hilal et al. |
| 5,350,104 | A | 9/1994 | Main et al. |
| 5,352,222 | A | 10/1994 | Rydell |
| 5,352,223 | A | 10/1994 | McBrayer et al. |
| 5,352,235 | A | 10/1994 | Koros et al. |
| 5,354,266 | A | 10/1994 | Snoke |
| 5,356,408 | A | 10/1994 | Rydell |
| 5,358,506 | A | 10/1994 | Green et al. |
| 5,364,001 | A | 11/1994 | Bryan |
| 5,364,409 | A | 11/1994 | Kuwabara et al. |
| 5,366,133 | A | 11/1994 | Geiste |
| 5,366,476 | A | 11/1994 | Noda |
| 5,368,015 | A | 11/1994 | Wilk |
| 5,368,607 | A | 11/1994 | Freitas |
| 5,380,321 | A | 1/1995 | Yoon |
| 5,383,880 | A | 1/1995 | Hooven |
| 5,389,098 | A | 2/1995 | Tsuruta et al. |
| 5,391,156 | A | 2/1995 | Hildwein et al. |
| 5,392,978 | A | 2/1995 | Velez et al. |
| 5,395,030 | A | 3/1995 | Kuramoto et al. |
| 5,395,033 | A | 3/1995 | Byrne et al. |
| 5,395,369 | A | 3/1995 | McBrayer et al. |
| 5,396,900 | A | 3/1995 | Slater et al. |
| 5,397,046 | A | 3/1995 | Savage et al. |
| 5,400,267 | A | 3/1995 | Denen et al. |
| D357,535 | S | 4/1995 | Grant et al. |
| 5,403,312 | A | 4/1995 | Yates et al. |
| 5,403,326 | A | 4/1995 | Harrison et al. |
| 5,403,327 | A | 4/1995 | Thornton et al. |
| 5,411,508 | A | 5/1995 | Bessler et al. |
| 5,413,267 | A | 5/1995 | Solyntjes et al. |
| 5,413,268 | A | 5/1995 | Green et al. |

(56) References Cited

U.S. PATENT DOCUMENTS

| | | |
|---|---|---|
| 5,415,334 A | 5/1995 | Williamson et al. |
| 5,425,705 A | 6/1995 | Evard et al. |
| 5,425,738 A | 6/1995 | Gustafson et al. |
| 5,425,745 A | 6/1995 | Green et al. |
| 5,431,322 A | 7/1995 | Green et al. |
| 5,431,645 A | 7/1995 | Smith et al. |
| 5,433,721 A | 7/1995 | Hooven et al. |
| 5,437,636 A | 8/1995 | Snoke et al. |
| 5,437,684 A | 8/1995 | Calabrese et al. |
| 5,441,507 A | 8/1995 | Wilk |
| 5,443,198 A | 8/1995 | Viola et al. |
| 5,443,475 A | 8/1995 | Auerbach et al. |
| 5,447,265 A | 9/1995 | Vidal et al. |
| 5,454,825 A | 10/1995 | Van Leeuwen et al. |
| 5,456,684 A | 10/1995 | Schmidt et al. |
| 5,460,182 A | 10/1995 | Goodman et al. |
| 5,464,404 A | 11/1995 | Abela et al. |
| 5,465,894 A | 11/1995 | Clark et al. |
| 5,467,911 A | 11/1995 | Tsuruta et al. |
| 5,472,132 A | 12/1995 | Savage et al. |
| 5,474,223 A | 12/1995 | Viola et al. |
| 5,476,206 A | 12/1995 | Green et al. |
| 5,482,054 A | 1/1996 | Slater et al. |
| 5,482,197 A | 1/1996 | Green et al. |
| 5,485,947 A | 1/1996 | Olson et al. |
| 5,487,499 A | 1/1996 | Sorrentino et al. |
| 5,487,500 A | 1/1996 | Knodel et al. |
| 5,496,269 A | 3/1996 | Snoke |
| 5,496,317 A | 3/1996 | Goble et al. |
| 5,514,134 A | 5/1996 | Rydell et al. |
| 5,518,163 A | 5/1996 | Hooven |
| 5,518,164 A | 5/1996 | Hooven |
| 5,520,634 A | 5/1996 | Fox et al. |
| 5,524,180 A | 6/1996 | Wang et al. |
| 5,527,313 A | 6/1996 | Scott et al. |
| 5,529,235 A | 6/1996 | Boiarski et al. |
| 5,531,687 A | 7/1996 | Snoke et al. |
| 5,533,661 A | 7/1996 | Main et al. |
| 5,535,937 A | 7/1996 | Boiarski et al. |
| 5,549,565 A | 8/1996 | Ryan et al. |
| 5,553,765 A | 9/1996 | Knodel et al. |
| 5,554,169 A | 9/1996 | Green et al. |
| 5,562,677 A | 10/1996 | Hildwein et al. |
| 5,562,702 A | 10/1996 | Huitema et al. |
| 5,569,274 A | 10/1996 | Rapacki et al. |
| 5,569,289 A | 10/1996 | Yoon |
| 5,571,116 A | 11/1996 | Bolanos et al. |
| 5,573,543 A | 11/1996 | Akopov et al. |
| 5,578,052 A | 11/1996 | Koros et al. |
| 5,580,067 A | 12/1996 | Hamblin et al. |
| 5,582,611 A | 12/1996 | Tsuruta et al. |
| 5,584,425 A | 12/1996 | Savage et al. |
| 5,588,579 A | 12/1996 | Schnut et al. |
| 5,591,186 A | 1/1997 | Wurster et al. |
| 5,591,196 A | 1/1997 | Marin et al. |
| 5,597,107 A | 1/1997 | Knodel et al. |
| 5,599,347 A | 2/1997 | Hart et al. |
| 5,603,443 A | 2/1997 | Clark et al. |
| 5,607,094 A | 3/1997 | Clark et al. |
| 5,609,285 A | 3/1997 | Grant et al. |
| 5,609,560 A | 3/1997 | Ichikawa et al. |
| 5,618,303 A | 4/1997 | Marlow et al. |
| 5,618,307 A | 4/1997 | Donlon et al. |
| 5,626,607 A | 5/1997 | Malecki et al. |
| 5,639,008 A | 6/1997 | Gallagher et al. |
| 5,651,780 A | 7/1997 | Jackson et al. |
| 5,653,374 A | 8/1997 | Young et al. |
| 5,665,100 A | 9/1997 | Yoon |
| 5,667,473 A | 9/1997 | Finn et al. |
| 5,667,478 A | 9/1997 | McFarlin et al. |
| 5,667,517 A | 9/1997 | Hooven |
| 5,667,526 A | 9/1997 | Levin |
| 5,676,674 A | 10/1997 | Bolanos et al. |
| 5,688,269 A | 11/1997 | Newton et al. |
| 5,692,668 A | 12/1997 | Schulze et al. |
| 5,693,031 A | 12/1997 | Ryan et al. |
| 5,709,335 A | 1/1998 | Heck |
| 5,711,472 A | 1/1998 | Bryan |
| 5,732,871 A | 3/1998 | Clark et al. |
| 5,732,872 A | 3/1998 | Bolduc et al. |
| 5,735,848 A | 4/1998 | Yates et al. |
| 5,735,849 A | 4/1998 | Baden et al. |
| 5,735,861 A | 4/1998 | Peifer et al. |
| 5,741,285 A | 4/1998 | McBrayer et al. |
| 5,749,885 A | 5/1998 | Sjostrom et al. |
| 5,749,893 A | 5/1998 | Vidal et al. |
| 5,752,644 A | 5/1998 | Bolanos et al. |
| 5,758,814 A | 6/1998 | Gallagher et al. |
| 5,762,458 A | 6/1998 | Wang et al. |
| 5,779,130 A | 7/1998 | Alesi et al. |
| 5,782,396 A | 7/1998 | Mastri et al. |
| 5,782,397 A | 7/1998 | Koukline |
| 5,792,135 A | 8/1998 | Madhani et al. |
| 5,797,835 A | 8/1998 | Green |
| 5,797,900 A | 8/1998 | Madhani et al. |
| 5,797,944 A | 8/1998 | Nobles et al. |
| 5,807,377 A | 9/1998 | Madhani et al. |
| 5,807,402 A | 9/1998 | Yoon |
| 5,814,044 A | 9/1998 | Hooven |
| 5,815,640 A | 9/1998 | Wang et al. |
| 5,817,113 A | 10/1998 | Gifford, III et al. |
| 5,823,956 A | 10/1998 | Roth et al. |
| 5,829,662 A | 11/1998 | Allen et al. |
| 5,836,503 A | 11/1998 | Ehrenfels et al. |
| 5,846,221 A | 12/1998 | Snoke et al. |
| 5,855,583 A | 1/1999 | Wang et al. |
| 5,855,590 A | 1/1999 | Malecki et al. |
| 5,857,996 A | 1/1999 | Snoke |
| 5,860,953 A | 1/1999 | Snoke et al. |
| 5,868,760 A | 2/1999 | McGuckin, Jr. |
| 5,871,471 A | 2/1999 | Ryan et al. |
| 5,878,193 A | 3/1999 | Wang et al. |
| 5,881,943 A | 3/1999 | Heck et al. |
| 5,893,875 A | 4/1999 | O'Connor et al. |
| 5,897,562 A | 4/1999 | Bolanos et al. |
| 5,907,664 A | 5/1999 | Wang et al. |
| 5,913,842 A | 6/1999 | Boyd et al. |
| 5,915,616 A | 6/1999 | Viola et al. |
| 5,925,055 A | 7/1999 | Adrian et al. |
| 5,931,848 A | 8/1999 | Saadat |
| 5,947,363 A | 9/1999 | Bolduc et al. |
| 5,951,549 A | 9/1999 | Richardson et al. |
| 5,954,259 A | 9/1999 | Viola et al. |
| 5,957,363 A | 9/1999 | Heck |
| 5,957,882 A | 9/1999 | Nita et al. |
| 5,957,884 A | 9/1999 | Hooven |
| 5,976,159 A | 11/1999 | Bolduc et al. |
| 5,984,919 A | 11/1999 | Hilal et al. |
| 5,989,215 A | 11/1999 | Delmotte et al. |
| 5,993,378 A | 11/1999 | Lemelson |
| 5,993,454 A | 11/1999 | Longo |
| 5,997,510 A | 12/1999 | Schwemberger |
| 6,001,108 A | 12/1999 | Wang et al. |
| 6,004,335 A | 12/1999 | Vaitekunas et al. |
| 6,007,512 A | 12/1999 | Hooven |
| 6,007,531 A | 12/1999 | Snoke et al. |
| 6,010,054 A | 1/2000 | Johnson et al. |
| 6,010,493 A | 1/2000 | Snoke |
| 6,017,322 A | 1/2000 | Snoke et al. |
| 6,017,354 A | 1/2000 | Culp et al. |
| 6,024,741 A | 2/2000 | Williamson, IV et al. |
| 6,063,095 A | 5/2000 | Wang et al. |
| 6,068,627 A | 5/2000 | Orszulak et al. |
| 6,074,402 A | 6/2000 | Peifer et al. |
| 6,083,163 A | 7/2000 | Wegner et al. |
| 6,086,600 A | 7/2000 | Kortenbach |
| 6,090,120 A | 7/2000 | Wright et al. |
| 6,099,466 A | 8/2000 | Sano et al. |
| 6,106,512 A | 8/2000 | Cochran et al. |
| 6,110,188 A | 8/2000 | Narciso, Jr. |
| 6,119,913 A | 9/2000 | Adams et al. |
| 6,126,058 A | 10/2000 | Adams et al. |
| 6,126,591 A | 10/2000 | McGarry et al. |
| 6,132,368 A | 10/2000 | Cooper |

(56) References Cited

U.S. PATENT DOCUMENTS

| | | |
|---|---|---|
| 6,162,220 A | 12/2000 | Nezhat |
| 6,165,191 A | 12/2000 | Shibata et al. |
| 6,174,324 B1 | 1/2001 | Egan et al. |
| 6,179,837 B1 | 1/2001 | Hooven |
| 6,193,129 B1 | 2/2001 | Bittner et al. |
| D438,617 S | 3/2001 | Cooper et al. |
| 6,201,984 B1 | 3/2001 | Funda et al. |
| 6,206,903 B1 | 3/2001 | Ramans |
| D441,076 S | 4/2001 | Cooper et al. |
| 6,209,773 B1 | 4/2001 | Bolduc et al. |
| 6,217,591 B1 | 4/2001 | Egan et al. |
| D441,862 S | 5/2001 | Cooper et al. |
| 6,231,587 B1 | 5/2001 | Makower |
| 6,244,809 B1 | 6/2001 | Wang et al. |
| 6,246,200 B1 | 6/2001 | Blumenkranz et al. |
| D444,555 S | 7/2001 | Cooper et al. |
| 6,264,087 B1 | 7/2001 | Whitman |
| 6,270,508 B1 | 8/2001 | Klieman et al. |
| 6,309,397 B1 | 10/2001 | Julian et al. |
| 6,312,435 B1 | 11/2001 | Wallace et al. |
| 6,315,184 B1 | 11/2001 | Whitman |
| 6,331,181 B1 | 12/2001 | Tierney et al. |
| 6,346,072 B1 | 2/2002 | Cooper |
| 6,348,061 B1 | 2/2002 | Whitman |
| 6,364,888 B1 | 4/2002 | Niemeyer et al. |
| 6,368,340 B2 | 4/2002 | Malecki et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,443,973 B1 | 9/2002 | Whitman |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,533,157 B1 | 3/2003 | Whitman |
| 6,790,217 B2 | 9/2004 | Schulze et al. |
| 7,695,485 B2 | 4/2010 | Whitman et al. |
| 8,512,359 B2 | 8/2013 | Whitman et al. |
| 2001/0016750 A1 | 8/2001 | Malecki et al. |
| 2001/0031975 A1 | 10/2001 | Whitman et al. |
| 2002/0032451 A1 | 3/2002 | Tierney et al. |
| 2002/0032452 A1 | 3/2002 | Tierney et al. |
| 2002/0042620 A1 | 4/2002 | Julian et al. |
| 2002/0045888 A1 | 4/2002 | Ramans et al. |
| 2002/0049454 A1 | 4/2002 | Whitman et al. |
| 2002/0055795 A1 | 5/2002 | Niemeyer et al. |
| 2002/0072736 A1 | 6/2002 | Tierney et al. |
| 2002/0165444 A1 | 11/2002 | Whitman |
| 2003/0105478 A1 | 6/2003 | Whitman et al. |
| 2003/0130677 A1 | 7/2003 | Whitman et al. |

FOREIGN PATENT DOCUMENTS

| | | |
|---|---|---|
| DE | 2903159 A1 | 7/1980 |
| DE | 3114135 A1 | 10/1982 |
| DE | 3300768 A1 | 7/1984 |
| DE | 4213426 A1 | 10/1992 |
| DE | 4312147 A1 | 10/1993 |
| DE | 4441333 A1 | 5/1996 |
| DE | 19626433 A1 | 1/1998 |
| EP | 0041022 A1 | 12/1981 |
| EP | 0116220 A1 | 8/1984 |
| EP | 0121474 A2 | 10/1984 |
| EP | 0142225 A1 | 5/1985 |
| EP | 0156774 A2 | 10/1985 |
| EP | 0203375 A2 | 12/1986 |
| EP | 0216532 A1 | 4/1987 |
| EP | 0293123 A2 | 11/1988 |
| EP | 0324166 A2 | 7/1989 |
| EP | 0324637 A1 | 7/1989 |
| EP | 0365153 A1 | 4/1990 |
| EP | 0369324 A1 | 5/1990 |
| EP | 0373762 A1 | 6/1990 |
| EP | 0399701 A1 | 11/1990 |
| EP | 0484677 A1 | 5/1992 |
| EP | 0514139 A2 | 11/1992 |
| EP | 0536903 A2 | 4/1993 |
| EP | 0539762 A1 | 5/1993 |
| EP | 0552050 A2 | 7/1993 |
| EP | 0552423 A2 | 7/1993 |
| EP | 0581400 A1 | 2/1994 |
| EP | 0593920 A1 | 4/1994 |
| EP | 0598579 A1 | 5/1994 |
| EP | 0621006 A1 | 10/1994 |
| EP | 0630612 A1 | 12/1994 |
| EP | 0634144 A1 | 1/1995 |
| EP | 0639349 A2 | 2/1995 |
| EP | 0653922 A1 | 5/1995 |
| EP | 0679367 A2 | 11/1995 |
| EP | 0705571 A1 | 4/1996 |
| EP | 0878169 A1 | 11/1998 |
| EP | 0947167 A1 | 10/1999 |
| FR | 2660851 A1 | 10/1991 |
| GB | 1082821 A | 9/1967 |
| GB | 1352554 A | 5/1974 |
| GB | 1452185 A | 10/1976 |
| GB | 2048685 A | 12/1980 |
| GB | 2165559 A | 4/1986 |
| GB | 2180455 A | 4/1987 |
| NL | 7711347 A | 4/1979 |
| SU | 659146 A1 | 4/1979 |
| WO | 8203545 A1 | 10/1982 |
| WO | 8300992 A1 | 3/1983 |
| WO | 9005489 A1 | 5/1990 |
| WO | 9005491 A2 | 5/1990 |
| WO | 9006085 A1 | 6/1990 |
| WO | 9107136 A1 | 5/1991 |
| WO | 9216141 A1 | 10/1992 |
| WO | 9308754 A1 | 5/1993 |
| WO | 9314706 A1 | 8/1993 |
| WO | 9518572 A1 | 7/1995 |
| WO | 9535065 A1 | 12/1995 |
| WO | 9712555 A2 | 4/1997 |
| WO | 9814129 A1 | 4/1998 |
| WO | 9920328 A2 | 4/1999 |
| WO | 9958076 A1 | 11/1999 |
| WO | 0072765 A1 | 12/2000 |
| WO | 0103587 A1 | 1/2001 |
| WO | 0108572 A1 | 2/2001 |
| WO | 01/17448 | 3/2001 |
| WO | 0135813 A1 | 5/2001 |
| WO | 0162163 A1 | 8/2001 |
| WO | 02058539 A2 | 8/2002 |

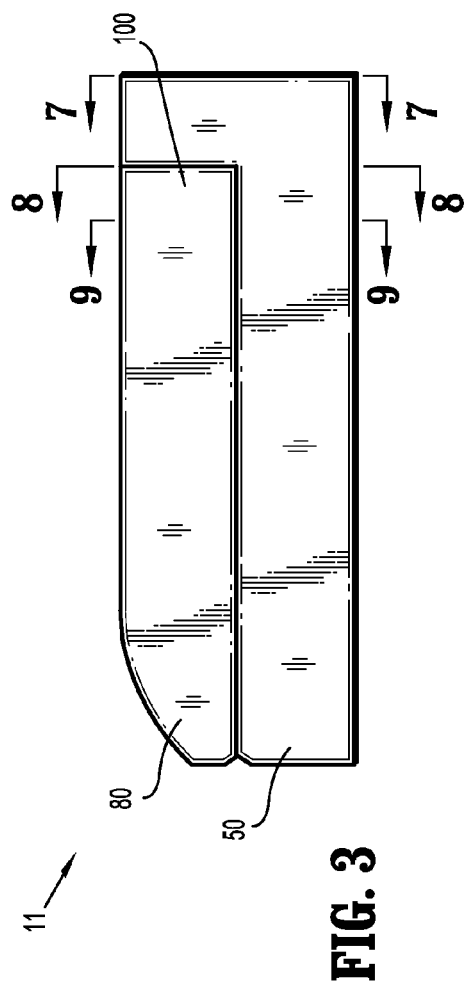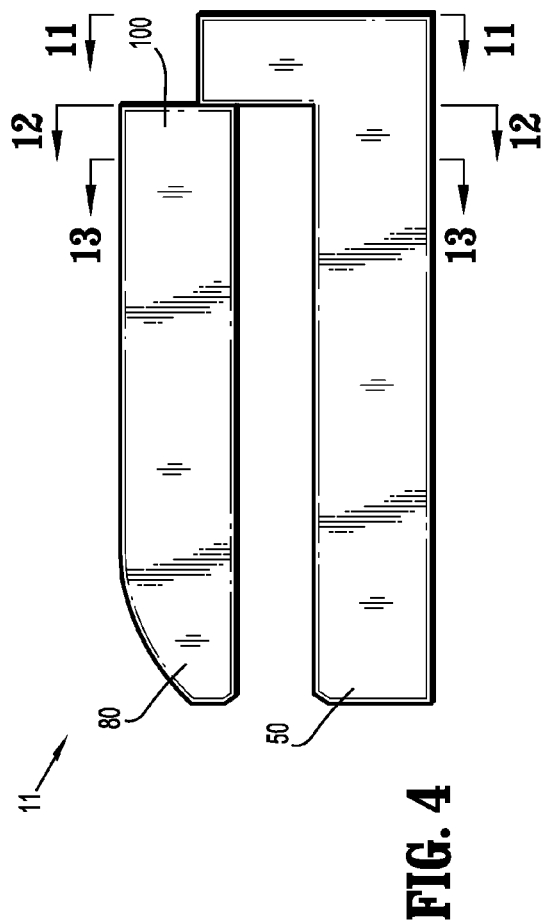

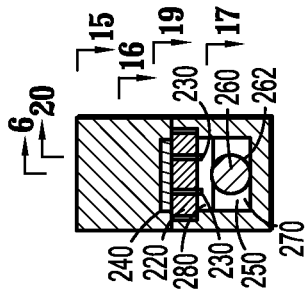
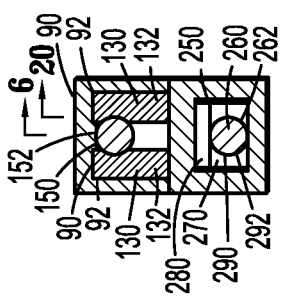
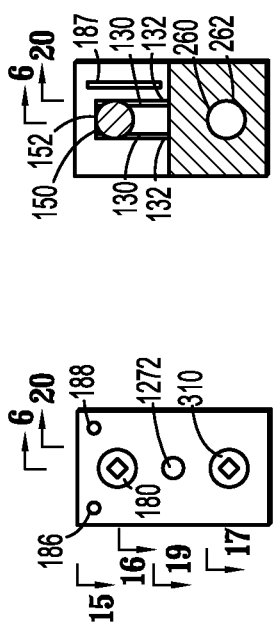
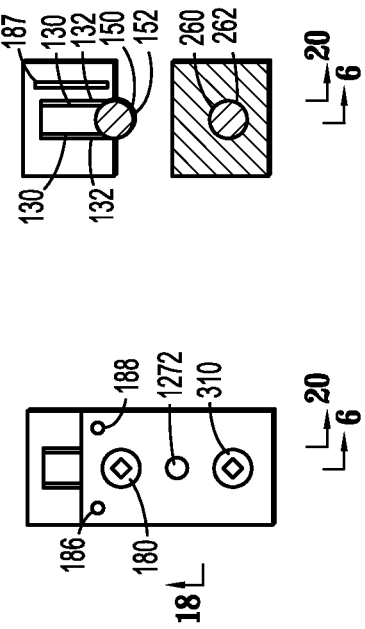

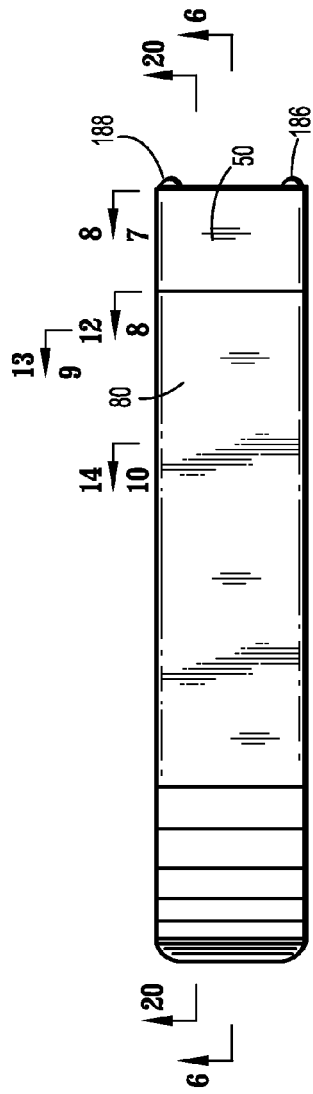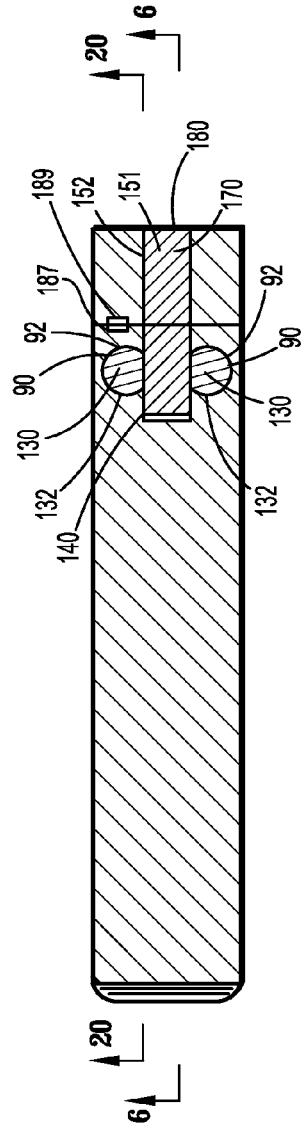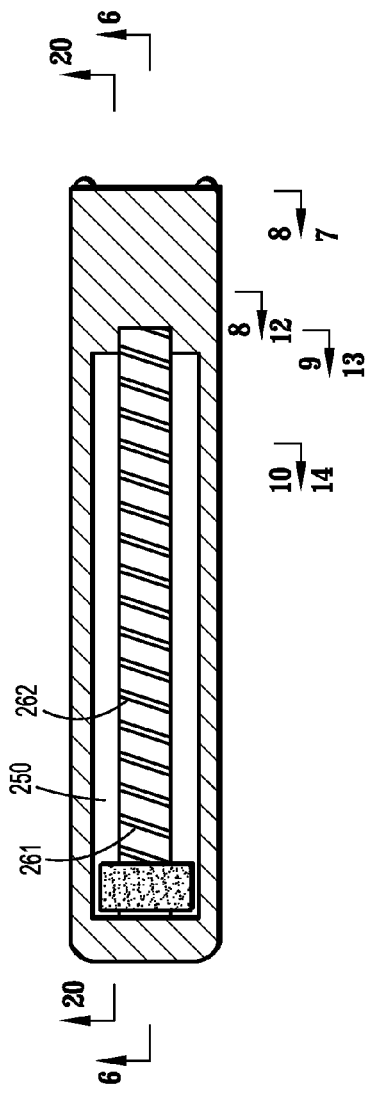

SURGICAL DEVICE

CROSS-REFERENCE TO RELATED APPLICATIONS

The present application is a Continuation Application claiming the benefit of and priority to U.S. patent application Ser. No. 13/207,697 (now U.S. Pat. No. 8,512,359), filed Aug. 11, 2011, which is a Continuation Application claiming the benefit of and priority to U.S. patent application Ser. No. 12/749,573 (now U.S. Pat. No. 8,021,373), filed Mar. 30, 2010, which is a Divisional Application claiming the benefit of and priority to U.S. patent application Ser. No. 09/999,546 (now U.S. Pat. No. 7,695,485), filed on Nov. 30, 2001, the entire contents of which are incorporated herein by reference.

The present application incorporates herein each of the following references as fully as if set forth in their entirety: U.S. patent application Ser. No. 09/887,789, filed on Jun. 22, 2001 and issued as U.S. Pat. No. 7,032,798 on Apr. 25, 2006; U.S. patent application Ser. No. 09/836,781, filed on Apr. 17, 2001 and issued as U.S. Pat. No. 6,981,941 on Jan. 3, 2006; U.S. patent application Ser. No. 09/723,715, filed on Nov. 28, 2000 and issued as U.S. Pat. No. 6,793,652 on Sep. 21, 2004; U.S. patent application Ser. No. 09/324,451, filed on Jun. 2, 1999 and issued as U.S. Pat. No. 6,315,184 on Nov. 13, 2001; U.S. patent application Ser. No. 09/324,452, filed on Jun. 2, 1999 and issued as U.S. Pat. No. 6,443,973 on Sep. 3, 2002; U.S. patent application Ser. No. 09/351,534, filed on Jul. 12, 1999 and issued as U.S. Pat. No. 6,264,087 on Jul. 24, 2001; U.S. patent application Ser. No. 09/510,923, filed on Feb. 22, 2000 and issued as U.S. Pat. No. 6,517,565 on Feb. 11, 2003; and U.S. patent application Ser. No. 09/510,927, filed on Feb. 22, 2000 and issued as U.S. Pat. No. 6,716,233 on Apr. 6, 2004.

FIELD OF THE INVENTION

The present invention relates to a surgical device. More specifically, the present invention relates to a linear clamping, cutting and stapling device for clamping, cutting and stapling tissue.

BACKGROUND INFORMATION

The literature is replete with descriptions of surgical devices. Applicant's co-pending U.S. patent application Ser. No. 09/887,789 (now U.S. Pat. No. 7,032,798) lists some of these surgical devices, such as U.S. Pat. No. 4,705,038 to Sjostrom et al.; U.S. Pat. No. 4,995,877 to Ams et al.; U.S. Pat. No. 5,249,583 to Mallaby; U.S. Pat. No. 5,383,880 to Hooven; U.S. Pat. No. 5,395,033 to Byrne et al.; U.S. Pat. No. 5,467,911 to Tsuruta et al.; U.S. Pat. Nos. 5,518,163, 5,518,164 and 5,667,517, all to Hooven; U.S. Pat. No. 5,653,374 to Young et al.; U.S. Pat. No. 5,779,130 to Alesi et al.; and U.S. Pat. No. 5,954,259 to Viola et al.

One type of surgical device is a linear clamping, cutting and stapling device. An example of such a device is shown and described in U.S. Pat. No. 6,264,087 issued on Jul. 24, 2001. Such a device may be employed in a surgical procedure to resect a cancerous or anomalous tissue from a gastrointestinal tract.

With respect to the structural features of the conventional linear clamping, cutting and stapling instrument which is shown in FIG. 1, the device includes a pistol grip-styled structure having an elongated shaft and distal portion. The distal portion includes a pair of scissors-styled gripping elements, which clamp the open ends of the colon closed. In this device, one of the two scissors-styled gripping elements, the anvil portion, moves or pivots relative to overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue, against the anvil portion, thereby sealing the previously opened end. The scissoring elements may be integrally formed with the shaft or may be detachable such that various scissoring and stapling elements may be interchangeable.

One problem with the foregoing surgical devices, and in particular with the foregoing linear clamping, cutting and stapling devices such as that illustrated in FIG. 1, is the tendency of the opposing jaws of the clamping mechanism to be urged apart during the operation of cutting and stapling the tissue. Another problem with the foregoing surgical devices, and in particular with the foregoing linear clamping, cutting and stapling devices such as that illustrated in FIG. 1, is that the devices are difficult to maneuver. Because a linear clamping, cutting and stapling device may be employed corporeally, e.g., inside the body of a patient, the device must be small enough to be maneuvered inside the body of a patient. Conventional linear clamping, cutting and stapling devices such as that illustrated in FIG. 1 have an overall length which increases the difficulty in maneuvering the device, especially inside the patient's body.

Still another problem with the foregoing surgical devices, and in particular with the foregoing linear clamping, cutting and stapling devices such as that illustrated in FIG. 1, is that the torque required to cut and staple a section of tissue is undesirably high, thereby causing stress in various components of the devices. For instance, in other linear clamping, cutting and stapling devices which move scissoring and stapling elements from the proximal end to the distal end, a high torque is required to move the scissoring and stapling elements when the scissoring and stapling elements are at the distal end. Thus, when the cutting and stapling element has traveled to the distal end of the jaws, the high torque causes stress in the scissoring and stapling elements, and driver mechanisms of the device.

SUMMARY OF THE INVENTION

The present invention, according to one example embodiment thereof, relates to a surgical device, which includes a first jaw and a second jaw disposed in opposed correspondence with the first jaw. The second jaw is mechanically coupled to the first jaw at a proximal end opposite a distal end. A cutting element, having a blade facing the proximal end, is disposed within the second jaw, and a first driver is configured to move the cutting element from the distal end to the proximal end of the second jaw to thereby cut a section of tissue disposed between the first and second jaws.

According to an example embodiment, the device may include a stapling element disposed within the second jaw, wherein the cutting element and the stapling element are contiguous so as to define a single cutting and stapling element, such as a wedge having a blade disposed thereon. As the wedge is moved from the distal end of the second jaw to the proximal end, the wedge urges staples against opposing staple guides disposed in the first jaw in order to staple a section of tissue while the blade cuts the section of tissue.

By moving the cutting and stapling element from the distal end of the mechanism to the proximal end during the cutting and stapling operation, the example embodiment may reduce the tendency of the upper and lower jaws to separate during operation of the device. Specifically, by moving the cutting and stapling element from the distal end of the mechanism to the proximal end during the cutting and stapling operation, there may be a resulting reduction in the distance between the upper and lower jaws at their distal ends.

In addition, by moving the cutting and stapling element from the distal end of the mechanism to the proximal end during the cutting and stapling operation, the example embodiment may reduce the torque which is required during the cutting and stapling operation, thereby reducing the stress which is experienced by various components of the surgical device. By housing the cutting and stapling elements at the distal end of the mechanism, the example embodiment may also reduce the length of the surgical device relative to a conventional linear clamping, cutting and stapling device, thereby improving the device's maneuverability, especially when employed inside the body of a patient, and may enable the stroke (e.g., the distance which can be cut and stapled) to be lengthened so as to clamp, cut and staple a larger section of tissue than a conventional linear clamping, cutting and stapling device.

BRIEF DESCRIPTION OF THE DRAWINGS

FIGS. 3 and 4 are side views of the closed and open dispositions, respectively, of a linear clamping, cutting and stapling attachment according to one example embodiment of the present invention;

FIGS. 7 to 14 are rear sectional views of the linear clamping, cutting and stapling attachment illustrated in FIGS. 3 to 6;

FIGS. 15 to 19 are bottom, top sectional, deep top sectional, bottom sectional, and top views, respectively, of the linear clamping, cutting and stapling attachment illustrated in FIGS. 3 to 14;

DETAILED DESCRIPTION

Figure 1:
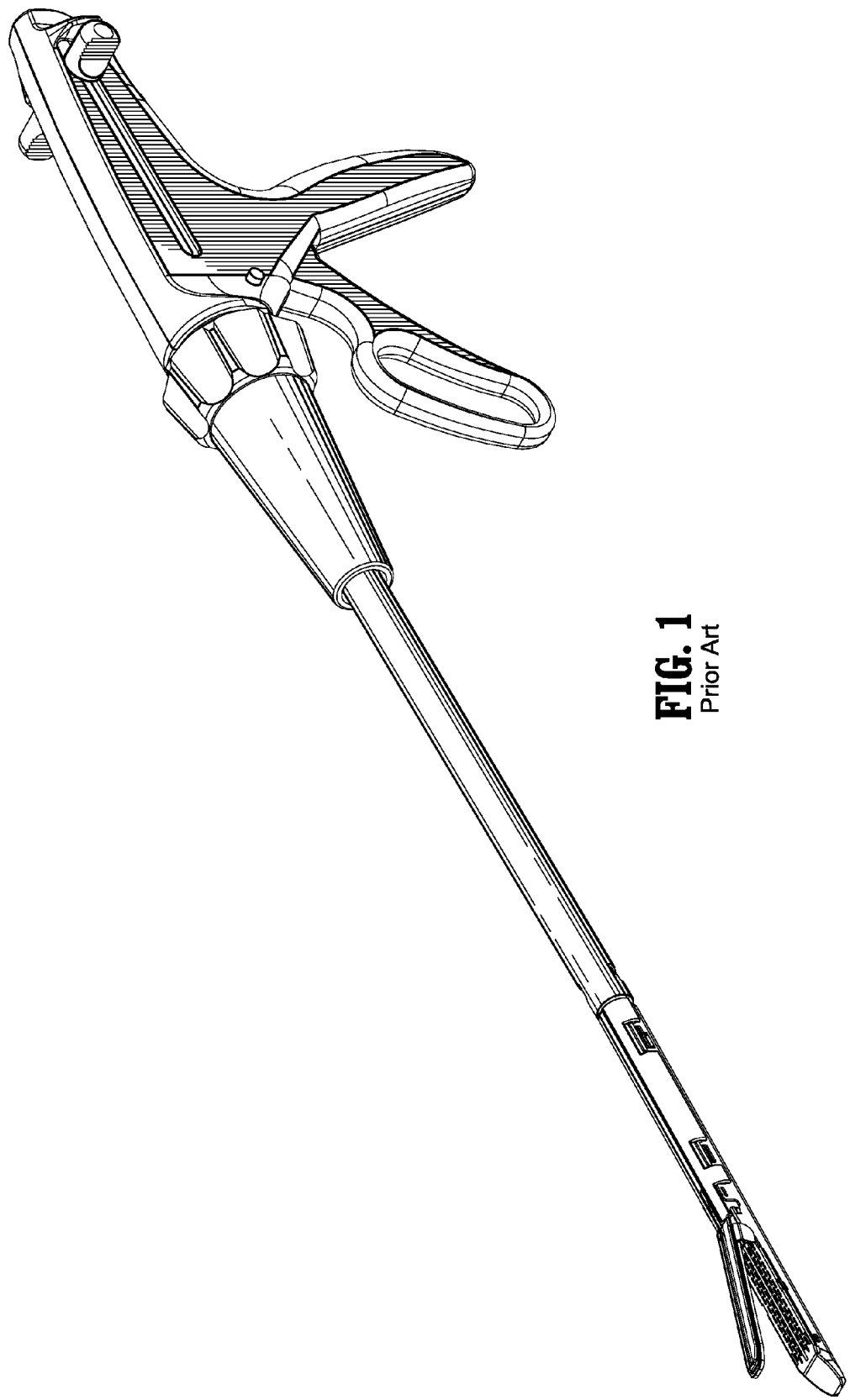
FIG. 1 is a perspective view of a conventional linear clamping, cutting and stapling device.

One example embodiment of a surgical device according to the present invention is illustrated in FIGS. 3 to 20. Referring to FIGS. 3 and 4, an example embodiment of the surgical device 11, e.g., a linear clamping, cutting and stapling device, is illustrated. In this embodiment, a device 11 includes a parallel separating jaw system having a lower jaw 50 in opposite correspondence to an upper jaw 80 having a proximal end 100. FIG. 3 illustrates the device 11 in a closed position, in which the lower jaw 50 and the upper jaw 80 are in contact at both their proximal and distal ends. FIG. 4 illustrates the device 11 in an open position, wherein the lower jaw 50 and the upper jaw 80 are separated. For the purposes of illustration only, FIGS. 3 to 20 illustrate the opposing jaws 50 and 80, which remain parallel relative to each other. In an alternative example embodiment, opposing jaws 50 and 80 may open and close in scissor-like fashion, wherein the proximal ends of opposing jaws 50 and 80 are mechanically connected by a hinge or other rotational element such that the upper jaw 50 is rotatably coupled to the lower jaw 80.

Figure 5:
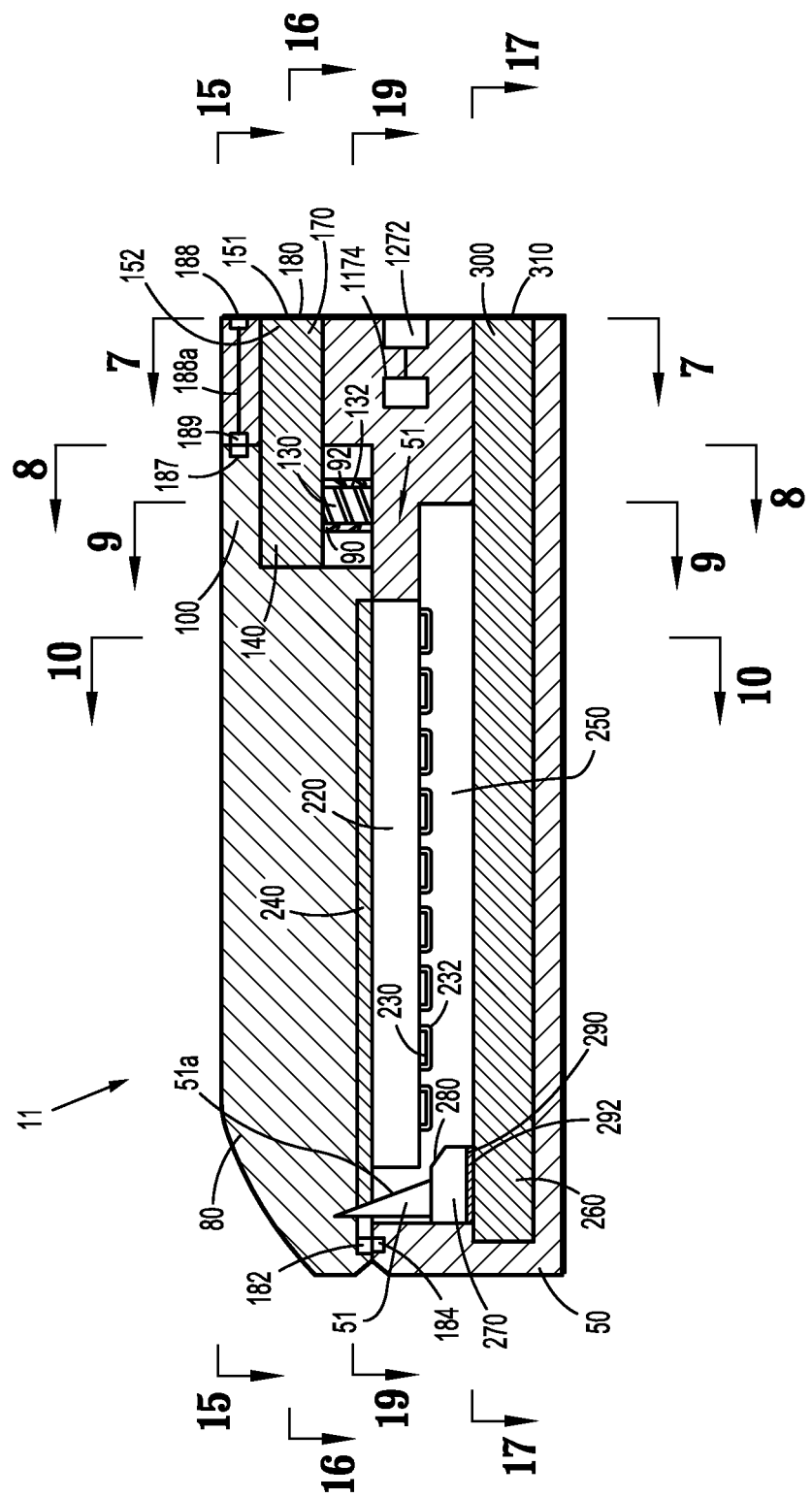
FIGS. 5 and 6 are side sectional views of the closed and open dispositions, respectively, of the linear clamping, cutting and stapling attachment illustrated in FIGS. 3 to 4.
Figure 6:
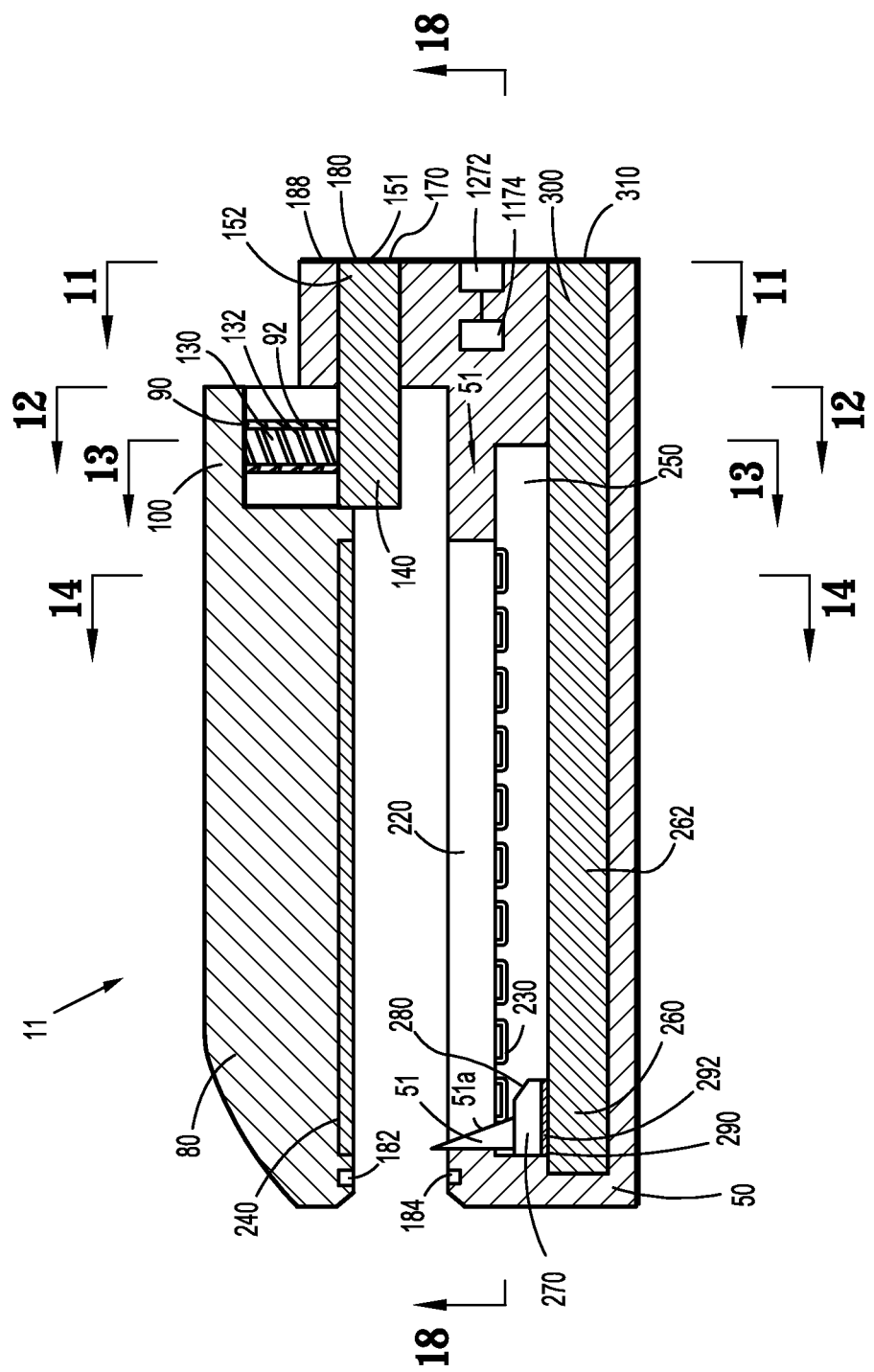

FIG. 5 is a side sectional view of the surgical device 11 in the closed position, corresponding to the view shown in FIG. 3. FIG. 6, on the other hand, is a side sectional view of the surgical device 11 in the open position, corresponding to the view shown in FIG. 4. Referring now to either FIG. 5 or FIG. 6, the proximal end 100 of the upper jaw 80 includes a pair of threaded vertical bores 90, through which extend a corresponding pair of vertical shafts 130. Inner threads 92 of the vertical bores 90 match outer threads 132 of the vertical shafts 130. The vertical shafts 130 engage a threaded upper horizontal shaft 151 at a distal end 140 of the upper horizontal shaft 151. The outer threads 152 of the upper horizontal shaft 151 interlock with the outer threads 132 of the vertical shafts 130. The upper horizontal shaft 151 includes an upper drive socket 180 at a proximal end 170.

Figure 5A:
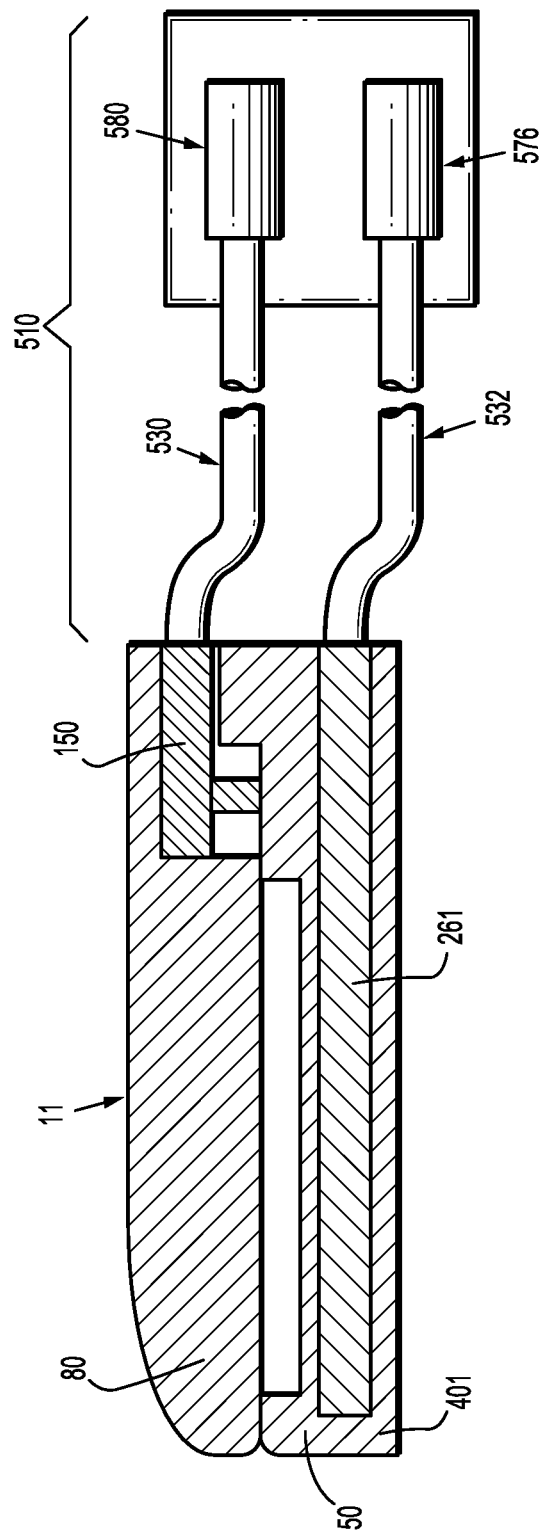
FIG. 5A is another sectional view of the closed disposition of the linear clamping, cutting and stapling attachment illustrated in FIGS. 3 to 6.

FIG. 5A is another sectional view of the closed disposition of the surgical device 11 illustrated in FIGS. 3 and 4, according to an example embodiment of the present invention. FIG. 5A illustrates the surgical device 11 coupled (removably or permanently) to an electro-mechanical surgical system 510. The surgical device 11 includes a first driver 261 which is coupled to a first motor 576 of the system 510 by a first drive shaft 532. As will be explained in more detail below, the first driver 261, when engaged by the system 510, operates to drive a cutting and stapling element within the lower jaw 50. In addition, the surgical device 11 includes a second driver 150, which is coupled to a second motor 580 of system 510 by a second drive shaft 530. As will be explained in more detail below, second driver 150, when engaged by system 510, operates to open and close upper jaw 80 relative to lower jaw 50.

Referring again to FIGS. 5 and 6, the surgical device 11 further includes a cutting element and a stapling element, which includes a wedge 270, having a blade 51 disposed thereon. In an alternative example embodiment, the cutting and stapling elements may be separately disposed. In the example embodiment, the blade 51 includes a cutting edge 51a that faces the proximal end 170 of the surgical device 11. In the lower jaw 50 is disposed a tray 220, which may be replaceable, housing one or more fasteners, e.g., staples 230, and in the upper jaw 80 is disposed one or more staple guides 240 corresponding to the staples 230. Each of the staples 230 includes a butt 232 protruding below the tray 220 and a pair of prongs 234 extending to the top of the tray 220. The surgical device 11 further includes a wedge guide or channel 250 extending beneath the tray 220. Within the channel 250 extends a threaded lower horizontal shaft 260 having outer threads 262. Upon the lower horizontal shaft 260 travels the wedge 270 having a sloped top face 280, a horizontal threaded bore 290 coaxial with the channel 250, having inner threads 292 matching the outer threads 262 of the lower horizontal shaft 260, and an upwardly extending blade member 51. As previously mentioned, the blade member 51 includes a cutting edge 51a facing the proximal end 170 of the surgical device 11. The lower horizontal shaft 260 has at a proximal end 300 a second drive socket 310.

In the example embodiment illustrated, the surgical device 11 also includes a first sensor electrode 182 electrically communicating via communication wires with a first contact pad 187 which electrically communicates with a second contact pad 189 via, e.g., direct contact. The second, contact pad 189 electrically communicates via the communication wires 188a with a first contact node 188. Similarly, the surgical device 11 further includes a second sensor electrode 184 electrically communicating via communication wires with a second contact node 186 (illustrated in FIG. 7). The contact nodes 186, 188 electrically communicate with communication wires (not shown) in the electro-mechanical drive component 510 to form a sensor circuit, such that when the upper jaw 80 and the lower jaw 50 are clamped together, the sensor electrodes 182, 184 are in contact, the sensor circuit is closed, and the operator is alerted via other circuit components (discussed in greater detail below) to the clamped position of the jaws 50, 80. The operator is therefore informed that it is safe and/or appropriate to begin a cutting and stapling process.

FIG. 7 is a rear sectional view, taken along the line 7-7, of the surgical device 11 illustrated in FIG. 5. FIG. 7 illustrates second contact node 186, as well as upper drive socket 180 for engaging a first drive shaft and lower drive socket 310 for engaging a second drive shaft. FIG. 7 also illustrates data connector 1272 coupled to a data memory unit 1174 (illustrated in FIGS. 5 and 6), the purpose and operation of which are discussed in greater detail below. FIG. 8 is a rear sectional view, taken along the line 8-8, of the surgical device 11 illustrated in FIG. 5. FIG. 9 is a rear sectional view, taken along the line 9-9, of the surgical device 11 illustrated in FIG. 5. FIG. 10 is a rear sectional view, taken along the line 10-10, of the surgical device 11 illustrated in FIG. 5.

FIG. 11 is a rear sectional view, taken along the line 11-11, of the surgical device 11 illustrated in Figure. FIG. 12 is a rear sectional view, taken along the line 12-12, of the surgical device 11 illustrated in FIG. 6. FIG. 13 is a rear view, taken along the line 13-13, of the surgical device 11 illustrated in FIG. 6. FIG. 14 is a rear view, taken along the line 14-14, of the surgical device 11 illustrated in FIG. 6.

Figure 18:
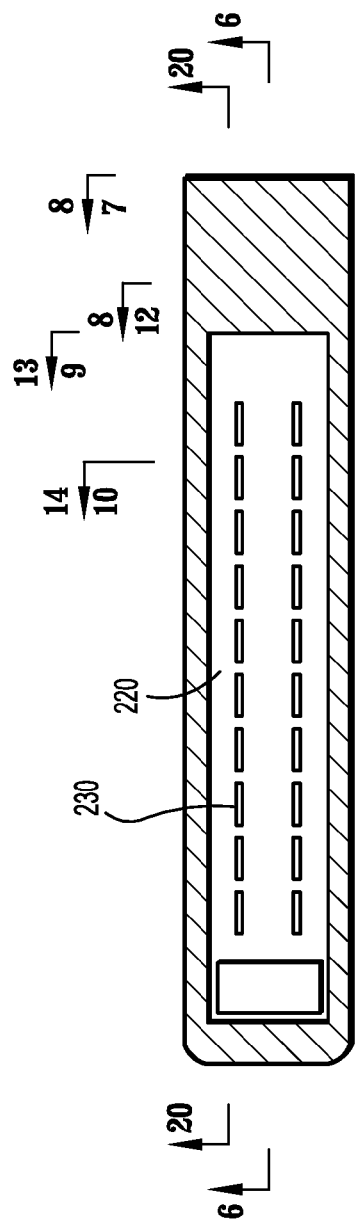
Figure 19:
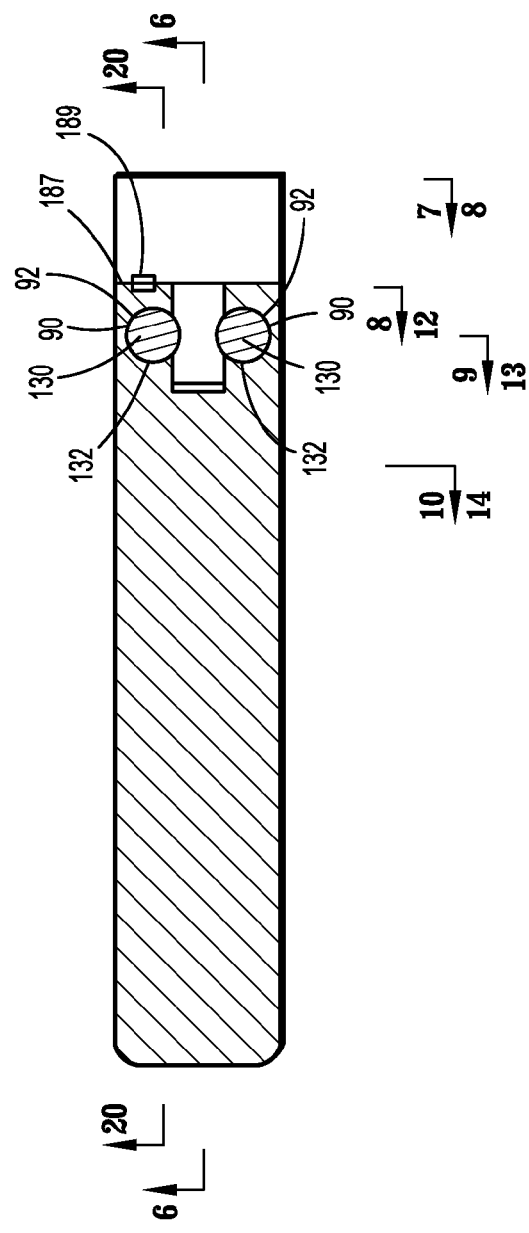
Figure 20:
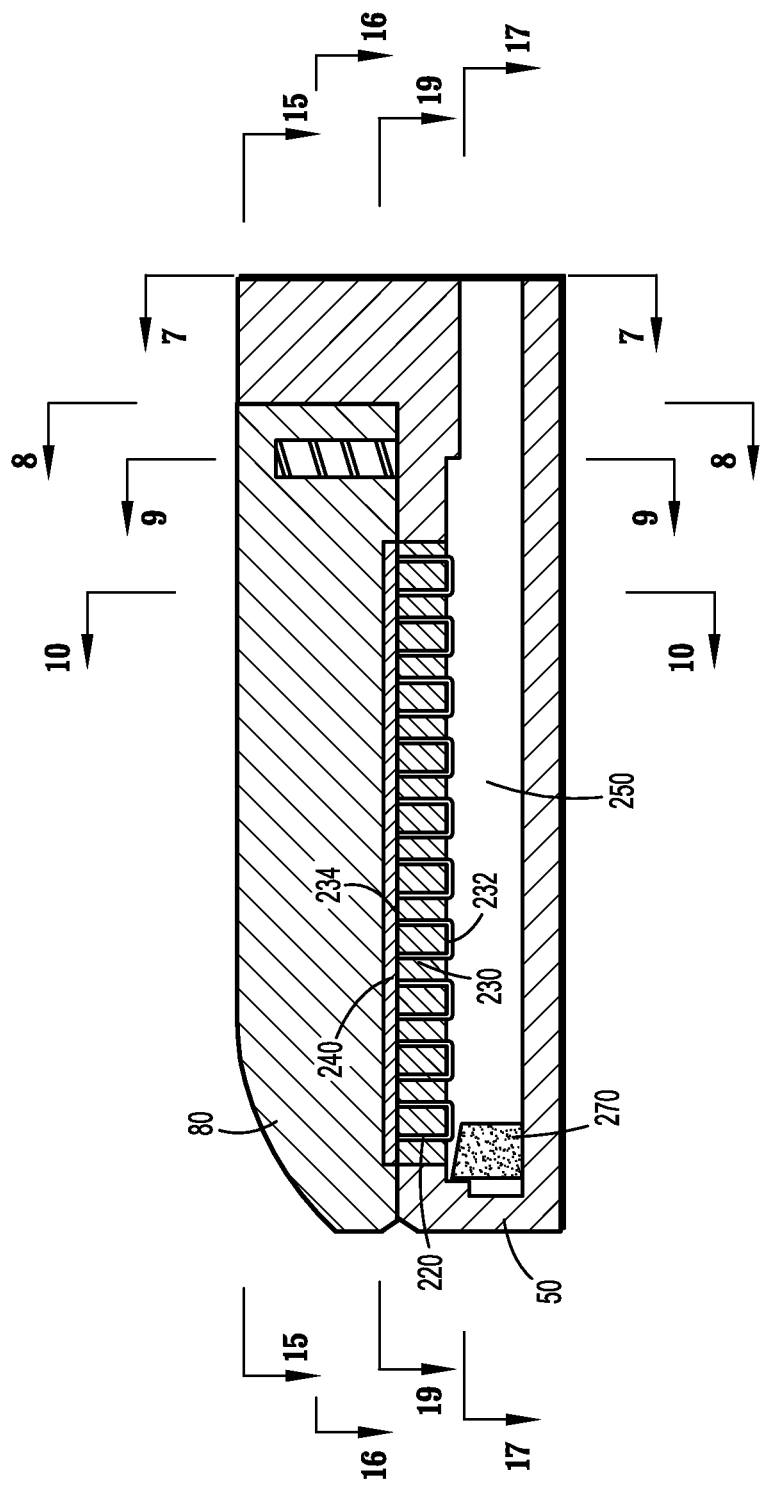
FIG. 20 is a side sectional of the linear clamping, cutting and stapling attachment illustrated in FIGS. 3 to 19.

FIG. 15 is a bottom view, taken along the line 15-15, of the surgical device 11 illustrated in FIGS. 5 and 6. FIG. 16 is a top sectional view, taken along the line 16-16, of the surgical device 11 illustrated in FIGS. 5 and 6. FIG. 17 is a deep top sectional view, taken along the line 17-17, of the surgical device 11 illustrated in FIGS. 5 and 6. FIG. 18 is a bottom sectional view, taken along the line 18-18, of the surgical device 11 illustrated in FIGS. 5 and 6. FIG. 19 is a top view, taken along the line 19-19, of the surgical device 11 illustrated in FIGS. 5 and 6. FIG. 20 is a side sectional view, taken along the line 20-20, of the surgical device 11 illustrated in FIGS. 5 and 6.

Each of the example embodiments described above include a wedge 270 having a blade 51 fixedly disposed thereon. According to another example embodiment of the present invention, the surgical device 11 includes a blade which is moveably coupled or mounted to a wedge so that the blade may move between a first position and a second position relative to the wedge. According to one embodiment, a first position of the blade relative to the wedge may be in a retracted position, whereas a second position of the blade relative to the wedge may be in an operable position, e.g., wherein the cutting edge of the blade faces the proximal end of the lower jaw 50 of the surgical device 11.

Figure 31:
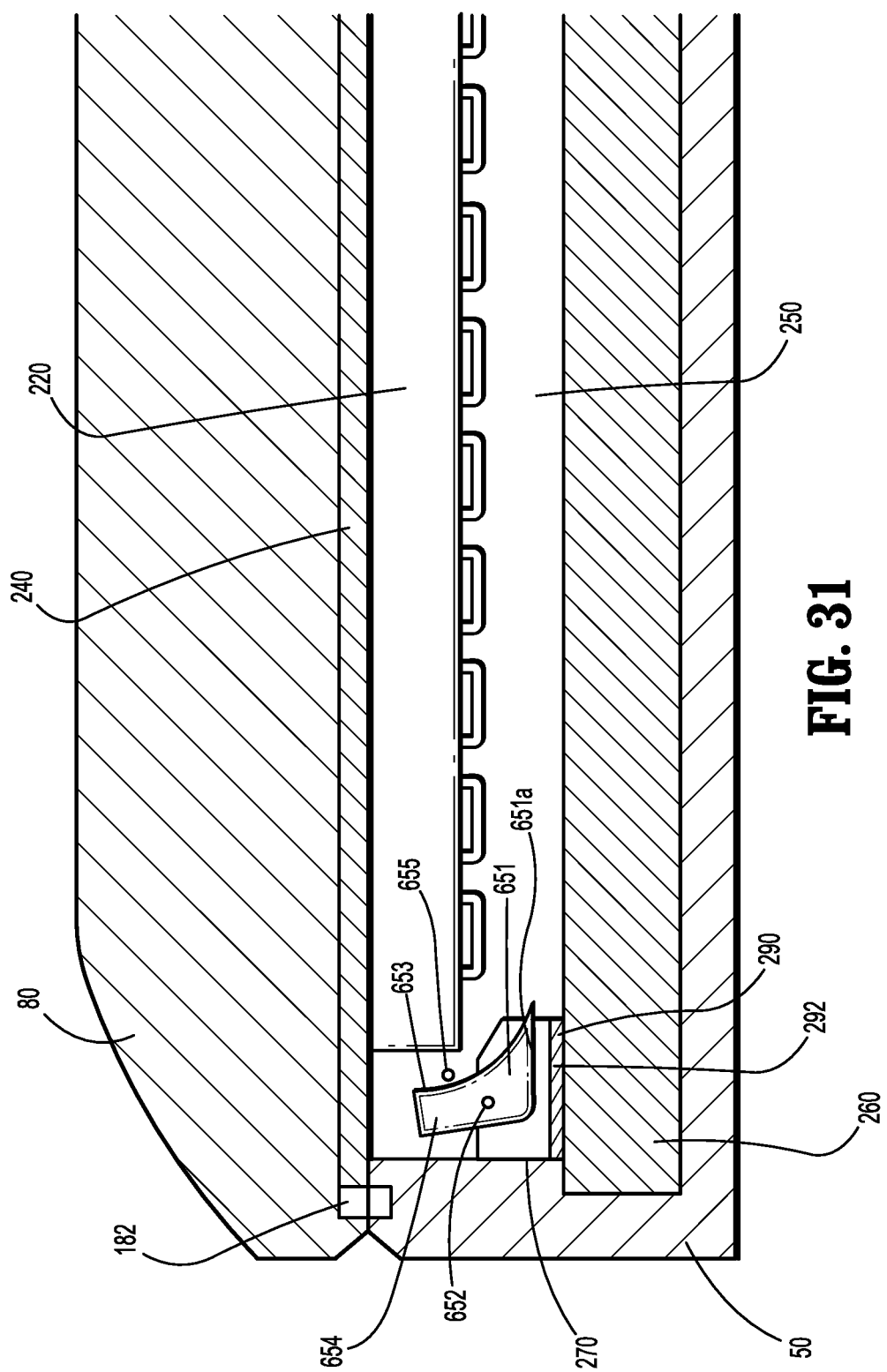
FIGS. 31 to 33 are side sectional views of the closed disposition of the linear clamping, cutting and stapling attachment illustrating a cutting element which is moveably coupled to the stapling element according to one example embodiment of the present invention.
Figure 32:
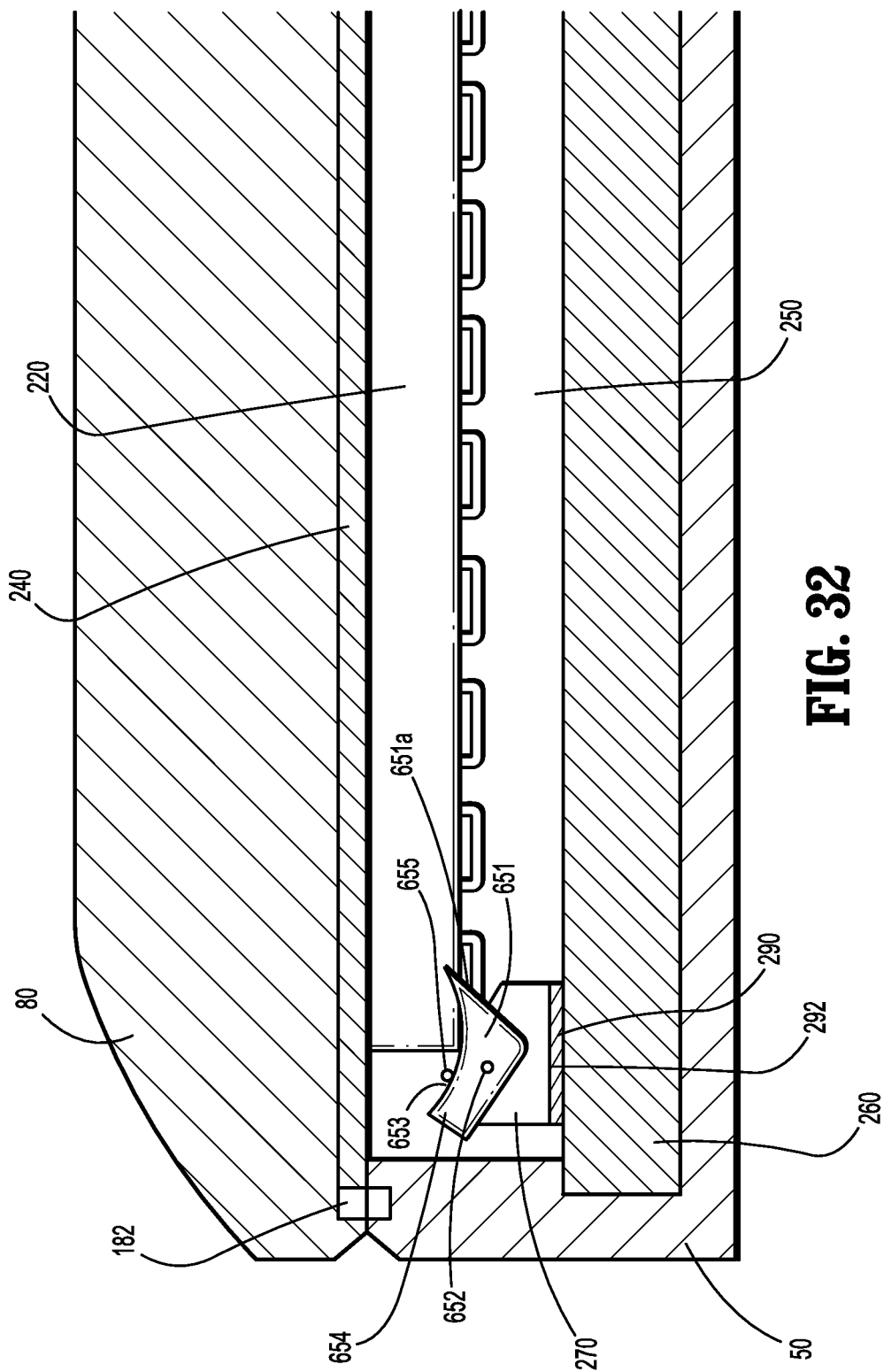
Figure 33:
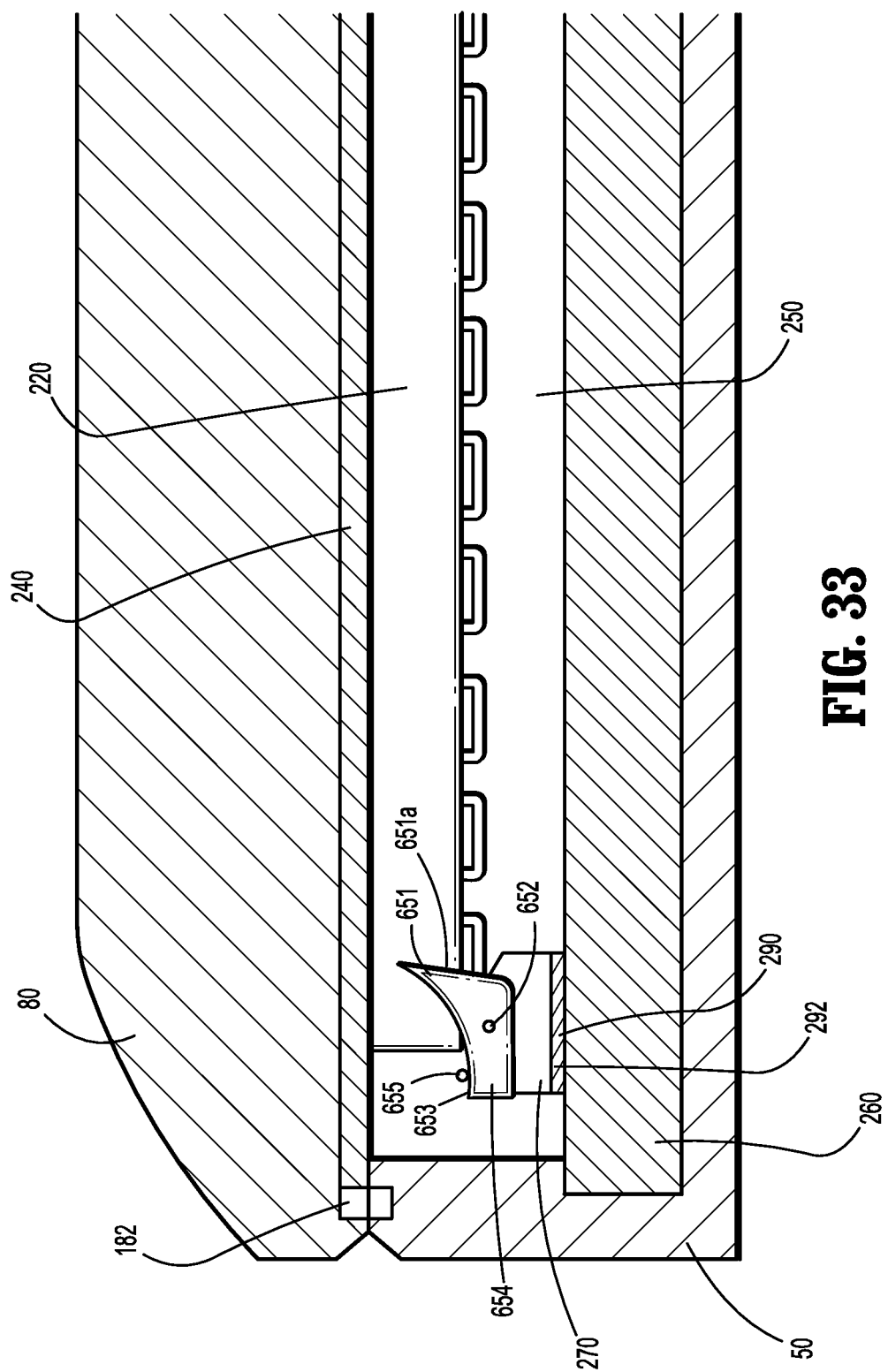

FIGS. 31 through 33 illustrate an example embodiment, wherein the surgical device 11 includes a blade 651 rotatably coupled to a wedge 670 so as to rotate between a first and a second position. The operation of the surgical device 11 shown in FIGS. 31 through 33 is discussed in greater detail below. FIGS. 31 through 33 illustrate the wedge 270 located at the distal end of the lower jaw 50. The blade 651 is rotatably mounted to the wedge 270 by a pivot member 652. The blade 651 includes a cutting edge 651a that is initially disposed in a retracted or down position, e.g., facing lower horizontal shaft 260. The blade 651 also includes a tail region 654 having an actuating pin receiving face 653 which initially faces the proximal end 170 of the surgical device 11. Located adjacent to actuating pin receiving face 653 is fixed actuating pin 655, which according to the example embodiment illustrated, is fixedly attached to lower jaw 50.

According to one example embodiment of the present invention, the surgical device 11 may be configured as an attachment to, or may be integral with, an electro-mechanical surgical system, such as electro-mechanical surgical system 510. In another embodiment, the surgical device may be configured as an attachment to, or may integral with, a purely mechanical device driver system, such as that illustrated in FIG. 1.

Figure 2:
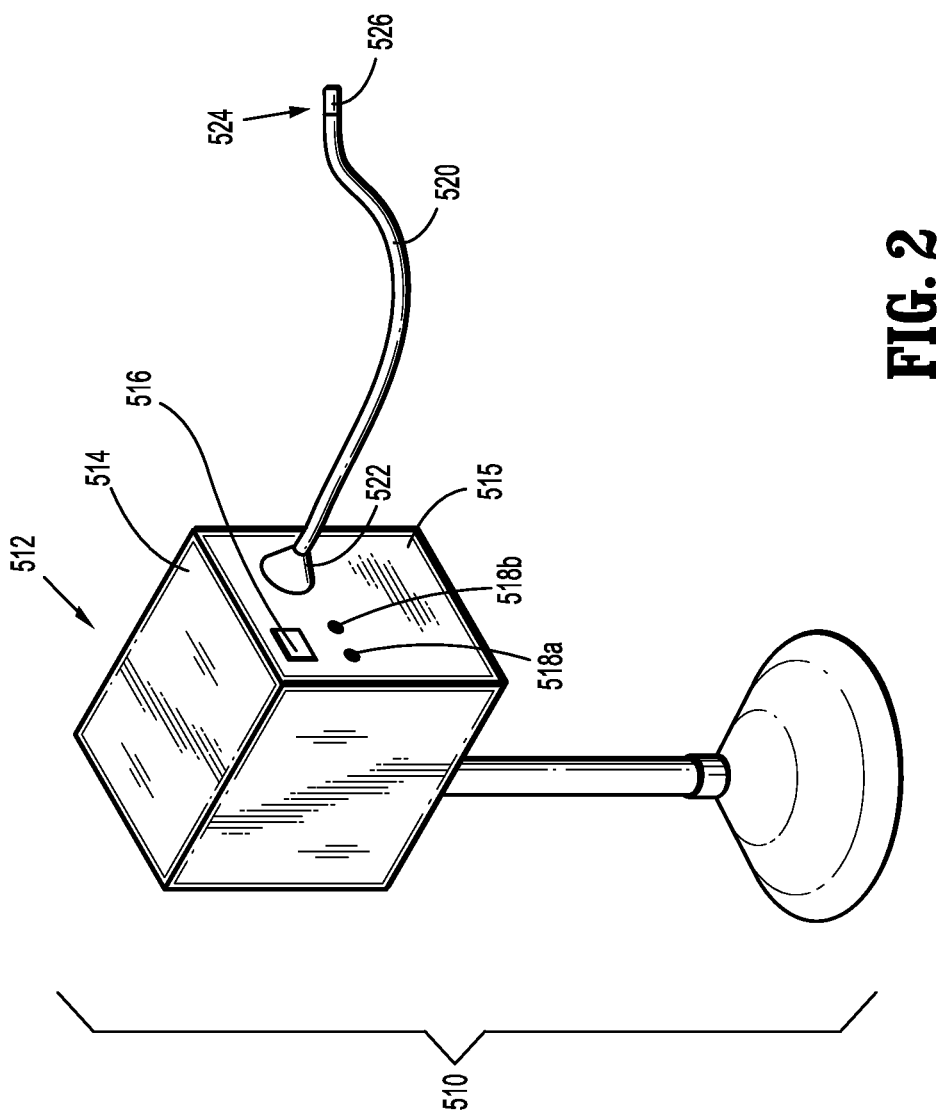
FIG. 2 is a perspective view of an electro-mechanical surgical system according to one example embodiment of the present invention.

FIG. 2 is a perspective view of an example embodiment of an electro-mechanical surgical system 510 according to the present invention. Electro-mechanical surgical system 510 may include, for example, a remote power console 512, which includes a housing 514 having a front panel 515. Mounted on front panel 515 are a display device 516 and indicators 518a, 518b, which are more fully described hereinbelow. A flexible shaft 520 may extend from housing 514 and may be detachably secured thereto via a first coupling 522. The distal end 524 of flexible shaft 520 may include a second coupling 526 adapted to detachably secure, e.g., the surgical device 11 described above, to the distal end 524 of flexible shaft 520. It is noted, however, that the second coupling 526 may also be adapted to detachably secure a different surgical instrument or attachment. In another embodiment, the distal end 524 of the flexible shaft 520 may permanently secure or be integral with a surgical instrument.

Figure 21:
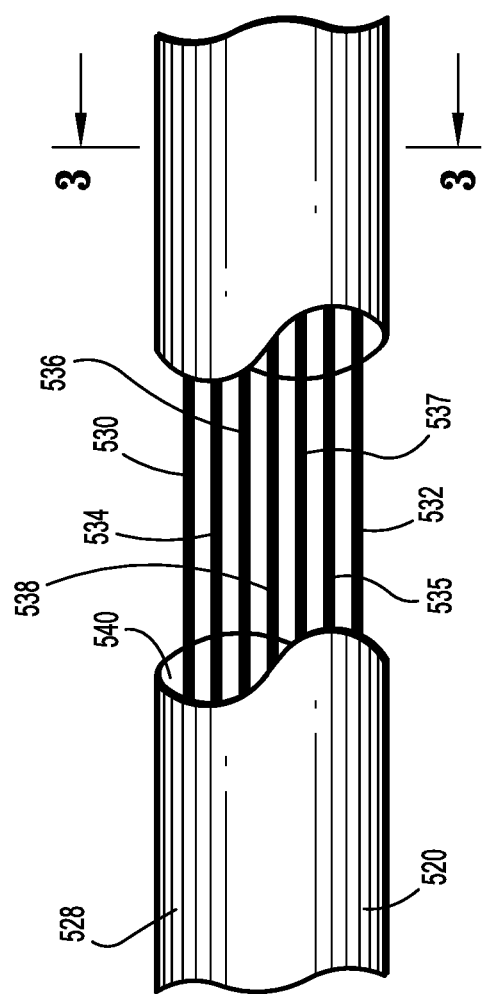
FIG. 21 is a side elevational view, partially in section, of a flexible shaft of the electro-mechanical surgical device according to one example embodiment of the present invention.
Figure 22:
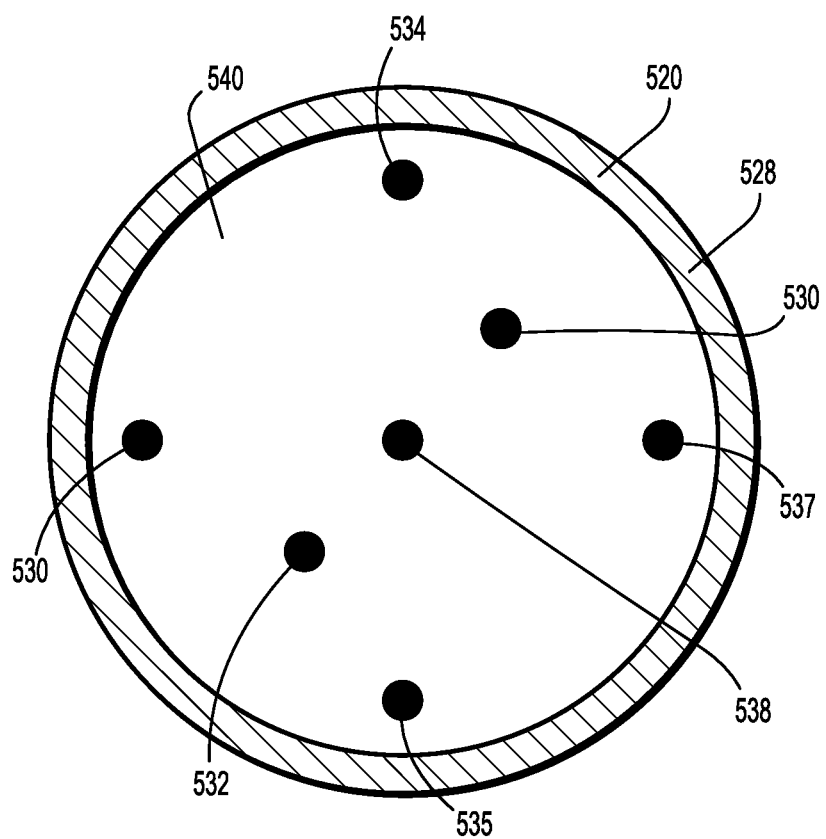
FIG. 22 is a cross-sectional view of the flexible shaft taken along the line 22-22 shown in FIG. 21.

Referring to FIG. 21, there is seen a side view, partially in section, of flexible shaft 520. According to one embodiment, flexible shaft 520 includes a tubular sheath 528, which may include a coating or other sealing arrangement to provide a fluid-tight seal between the interior channel 540 thereof and the environment. Sheath 528 may be formed of a tissue-compatible, sterilizable elastomeric material. The sheath 528 may also be formed of a material that is autoclavable. Disposed within the interior channel 540 of flexible shaft 520, and extending along the entire length thereof, may be a second rotatable drive shaft 530, a first rotatable drive shaft 532, a first steering cable 534, a second steering cable 535, a third steering cable 536, a fourth steering cable 537 and a data transfer cable 538. FIG. 22 is a cross-sectional view of flexible shaft 520 taken along the line 22-22 shown in FIG. 21 and further illustrates the several cables 530, 532, 534, 535, 536, 537, 538. Each distal end of the steering cables 534, 535, 536, 537 is affixed to the distal end 524 of the flexible shaft 520. Each of the several cables 530, 532, 534, 535, 536, 537, 538 may be contained within a respective sheath.

The second rotatable drive shaft 530 and the first rotatable drive shaft 532 may be configured, for example, as highly flexible drive shafts, such as, for example, braided or helical drive cables. It should be understood that such highly flexible drive cables have limited torque transmission characteristics and capabilities. It should also be understood that the surgical device 11 (or other attachments connected to the flexible shaft 520) may require a higher torque input than the torque transmittable by the drive shafts 530, 532. The drive shafts 530, 532 may thus be configured to transmit low torque but high speed, the high speed/low torque being converted to low speed/high torque by gearing arrangements disposed, for example, at the distal end and/or the proximal end of the drive flexible shaft 520, in the surgical instrument or attachment and/or in the remote power console 512. It should be appreciated that such gearing arrangement(s) may be provided at any suitable location along the power train between the motors disposed in the housing 514 and the attached surgical instrument or other attachment connected to the flexible shaft 520. Such gearing arrangement(s) may include, for example, a spur gear arrangement, a planetary gear arrangement, a harmonic gear arrangement, cycloidal drive arrangement, an epicyclic gear arrangement, etc.

Figure 23:
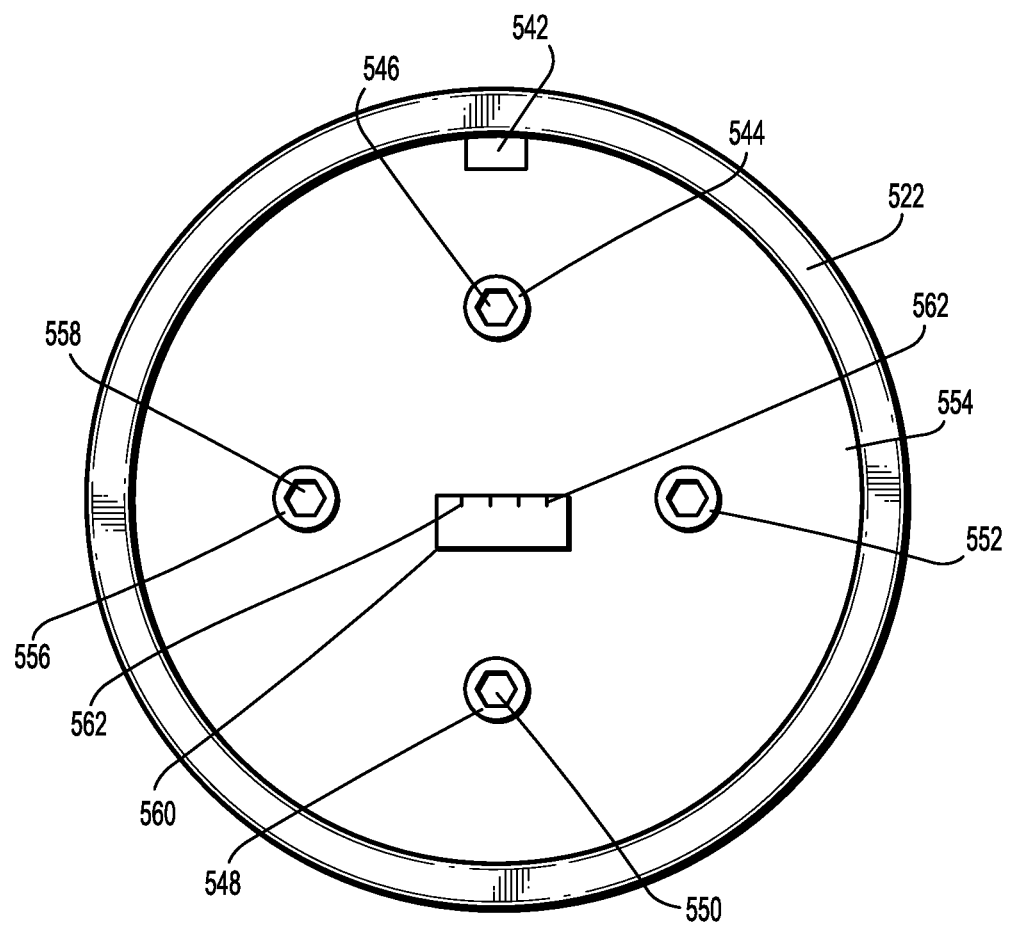
FIG. 23 is a rear end view of a first coupling of the flexible shaft illustrated in FIG. 21.

Referring now to FIG. 23, there is seen a rear end view of first coupling 522. First coupling 522 includes a first connector 544, a second connector 548, a third connector 552 and a fourth connector 556, each rotatably secured to first coupling 522. Each of the connectors 544, 548, 552, 556 includes a respective recess 546, 550, 554, 558. As shown in FIG. 23, each recess 546, 550, 554, 558 may be hexagonally shaped. It should be appreciated, however, that the recesses 546, 550, 554, 558 may have any shape and configuration to non-rotatably couple and rigidly attach the connectors 544, 548, 552, 556 to respective drive shafts of the motor arrangement contained within the housing 512, as more fully described below. It should be appreciated that complementary projections may be provided on respective drive shafts of the motor arrangement to thereby drive the drive elements of the flexible shaft 520 as described below. It should also be appreciated that the recesses may be provided on the drive shafts and complementary projections may be provided on the connectors 544, 548, 552, 556. Any other coupling arrangement configured to non-rotatably and releasably couple the connectors 544, 548, 552, 556 and the drive shafts of the motor arrangement may be provided.

One of the connectors 544, 548, 552, 556 is non-rotatably secured to the second drive shaft 530, and another one of the connectors 544, 548, 552, 556 is non-rotatably secured to the first drive shaft 532. The remaining two of the connectors 544, 548, 552, 556 engage with transmission elements configured to apply tensile forces on the steering cables 534, 535, 536, 537 to thereby steer the distal end 524 of the flexible shaft 520. The data transfer cable 538 is electrically and logically connected with data connector 560. Data connector 560 includes, for example, electrical contacts 562, corresponding to and equal in number to the number of individual wires contained in the data cable 538. First coupling 522 includes a key structure 542 to properly orient the first coupling 522 to a mating and complementary coupling arrangement disposed on the housing 512. Such key structure 542 may be provided on either one, or both, of the first coupling 522 and the mating and complementary coupling arrangement disposed on the housing 512. First coupling 522 may include a quick-connect type connector, which may use, for example, a simple pushing motion to engage the first coupling 522 to the housing 512. Seals may be provided in conjunction with any of the several connectors 544, 548, 552, 556, 560 to provide a fluid-tight seal between the interior of first coupling 522 and the environment.

Figure 24:
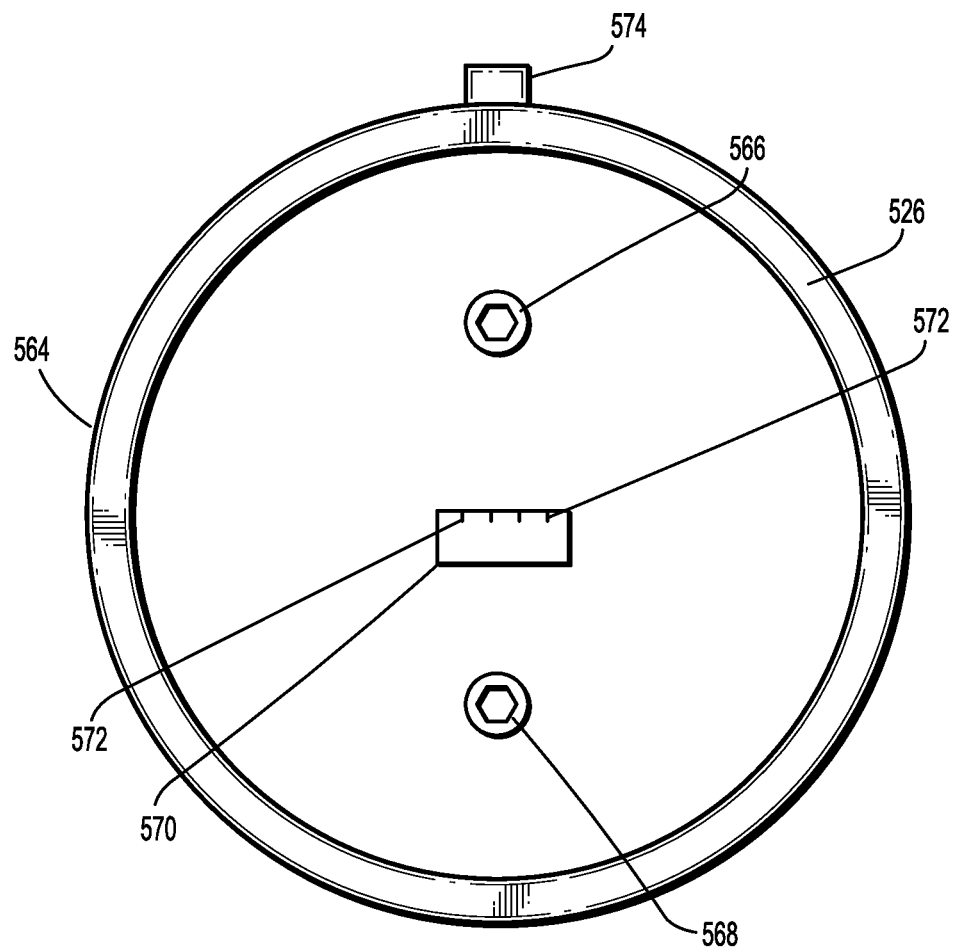
FIG. 24 is a front end view of a second coupling of the flexible shaft illustrated in FIG. 21.

Referring now to FIG. 24, there is seen a front end view of the second coupling 526 of flexible shaft 520. In the example embodiment, the second coupling 526 includes a first connector 566 and a second connector 568, each being rotatably secured to the second coupling 526 and each being non-rotatably secured to a distal end of a respective one of the first and second drive shafts 532, 530. A quick-connect type fitting 564 is provided on the second coupling 526 for detachably securing the device 11 thereto. The quick-connect type fitting 564 may be, for example, a rotary quick-connect type fitting, a bayonet type fitting, etc. A key structure 574 is provided on the second coupling 526 for properly aligning the device 11 to the second coupling 526. The key structure or other arrangement for properly aligning the device 11 to the flexible shaft 520 may be provided on either one, or both, of the second coupling 526 and the device 11. In addition, the quick-connect type fitting may be provided on the device 11. A data connector 570, having electrical contacts 572, is also provided in the second coupling 526. Like the data connector 560 of first coupling 522, the data connector 570 of second coupling 526 includes contacts 572 electrically and logically connected to the respective wires of data transfer cable 538 and contacts 562 of data connector 560. Seals may be provided in conjunction with the connectors 566, 568, 570 to provide a fluid-tight seal between the interior of second coupling 526 and the environment.

Disposed within housing 514 of the remote power console 512 are electro-mechanical driver elements configured to drive the drive shafts 530, 532 and the steering cables 534, 535, 536, 537 to thereby operate the electro-mechanical surgical system 510 and the linear clamping, cutting and stapling device 11 attached to the second coupling 526. In the example embodiment illustrated schematically in FIG. 25, five electric motors 576, 580, 584, 590, 596, each operating via a power source, may be disposed in the remote power console 512. It should be appreciated, however, that any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors.

Figure 25:
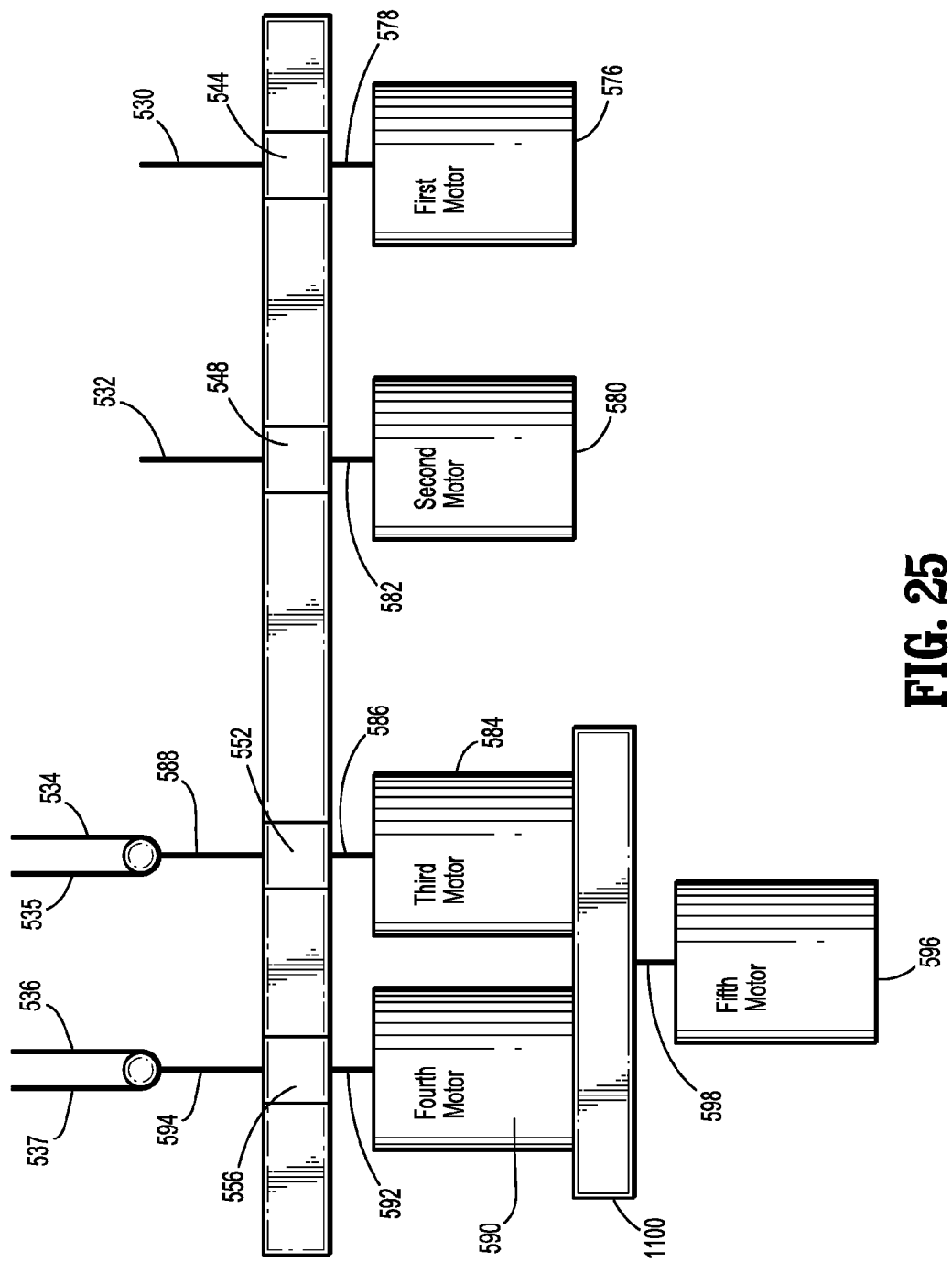
FIG. 25 is a schematic view illustrating a motor arrangement of the electro-mechanical surgical device illustrated in FIG. 2.

FIG. 25 illustrates schematically one possible arrangement of motors. An output shaft 578 of a first motor 576 engages with the first connector 544 of the first coupling 522 when the first coupling 522, and, therefore, flexible shaft 520, is engaged with the housing 514 to thereby drive the second drive shaft 530 and first connector 566 of second coupling 526. Similarly, an output shaft 582 of a second motor 580 engages the second connector 548 of first coupling 522 when first coupling 522, and, therefore, flexible shaft 520 is engaged with the housing 514 to thereby drive the first drive shaft 532 and second connector 568 of second coupling 526. An output shaft 586 of a third motor 584 engages the third connector 552 of the first coupling 522 when the first coupling 522, and, therefore, flexible shaft 520, is engaged with the housing 514 to thereby drive the first and second steering cables 534, 535 via a first pulley arrangement 588. An output shaft 592 of a fourth motor 590 engages the fourth connector 556 of the first coupling 522 when the first coupling 522, and, therefore, flexible shaft 520, is engaged with the housing 514 to thereby drive the third and fourth steering cables 536, 537 via a second pulley arrangement 594. The third and fourth motors 584, 590 may be secured on a carriage 1100, which is selectively movable via an output shaft 598 of a fifth motor 596 between a first position and a second position to selectively engage and disengage the third and fourth motors 584, 590 with the respective pulley arrangement 588, 594 to thereby permit the flexible shaft 520 to become taut and steerable or limp as necessary. It should be appreciated that other mechanical, electrical or electro-mechanical mechanisms may be used to selectively engage and disengage the steering mechanism. The motors may be arranged and configured as described, for example, in U.S. patent application Ser. No. 09/510,923 (now U.S. Pat. No. 6,517,565), entitled "A Carriage Assembly for Controlling a Steering Wire Mechanism Within a Flexible Shaft," which is hereby incorporated by reference herein as fully as if set forth in its entirety.

It should be appreciated, that any one or more of the motors 576, 580, 584, 590, 596 may be high-speed/low-torque motors or low-speed/high-torque motors. As indicated above, the second rotatable drive shaft 530 and the first rotatable drive shaft 532 may be configured to transmit high speed and low torque. Thus, the first motor 576 and the second motor 580 may be configured as high-speed/low-torque motors. Alternatively, the first motor 576 and the second motor 580 may be configured as low-speed/high-torque motors with a torque-reducing/speed-increasing gear arrangement disposed between the first motor 576 and the second motor 580 and a respective one of the second rotatable drive shaft 530 and the first rotatable drive shaft 532. Such torque-reducing/speed-increasing gear arrangement may include, for example, a spur gear arrangement, a planetary gear arrangement, a harmonic gear arrangement, cycloidal drive arrangement, an epicyclic gear arrangement, etc. It should be appreciated that any such gear arrangement may be disposed within the remote power console 512 or in the proximal end of the flexible shaft 520, such as, for example, in the first coupling 522. It should be appreciated that the gear arrangement(s) are provided at the distal and/or proximal ends of the second rotatable drive shaft 530 and/or the first rotatable drive shaft 532 to prevent windup and breakage thereof.

Figure 26:
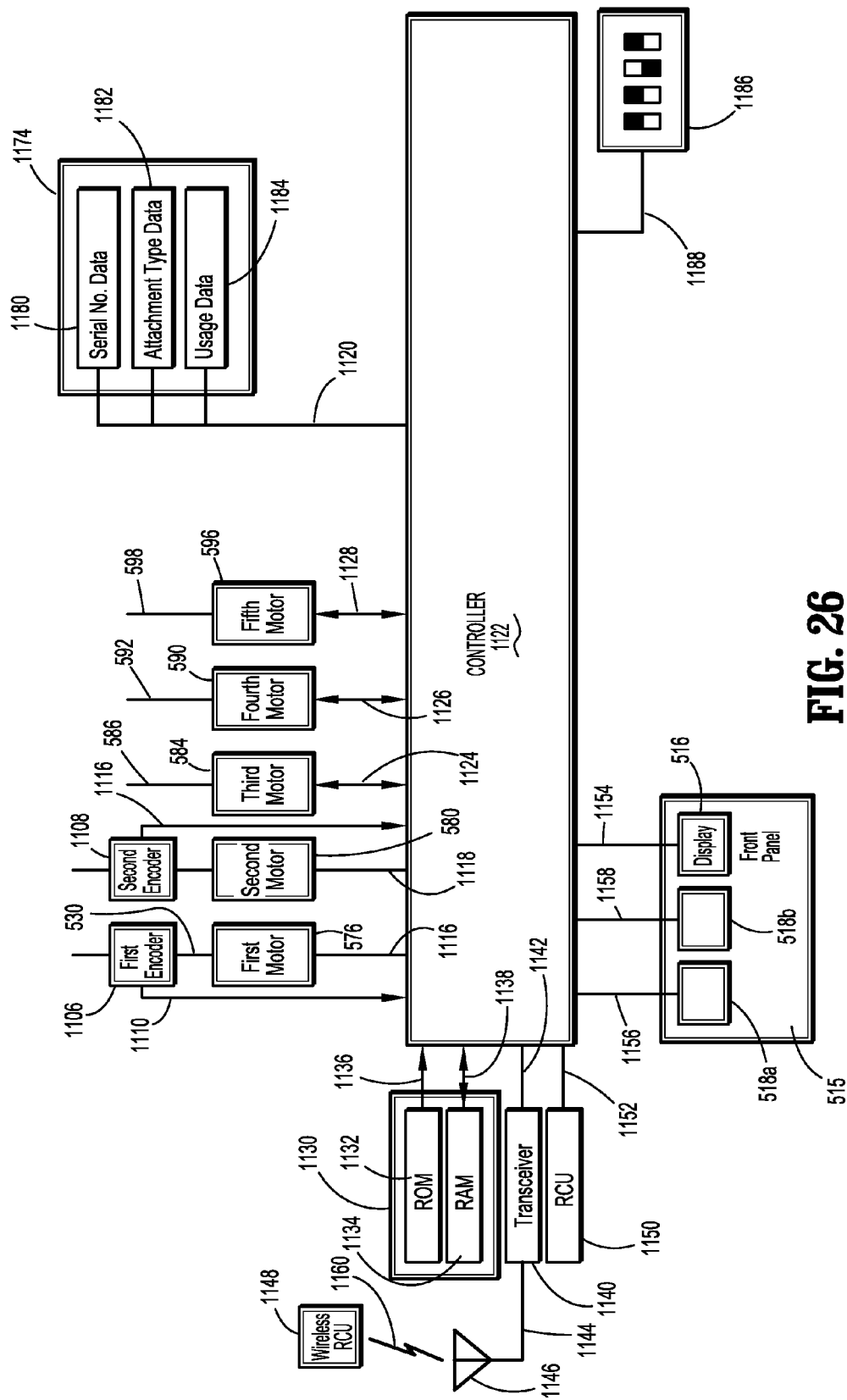
FIG. 26 is a schematic view of the electro-mechanical surgical device illustrated in FIG. 2.

Referring now to FIG. 26, there is seen a schematic view of the example electro-mechanical surgical system 510. A controller 1122 is provided in the housing 514 of remote power console 512 and is configured to control all functions and operations of the electro-mechanical surgical system 510 and the linear clamping, cutting and stapling device 11 attached to the flexible shaft 520. A memory unit 1130 is provided and may include memory devices, such as, a ROM component 1132 and/or a RAM component 1134. ROM component 1132 is in electrical and logical communication with controller 1122 via line 1136, and RAM component 1134 is in electrical and logical communication with controller 1122 via line 1138. RAM component 1134 may include any type of random-access memory, such as, for example, a magnetic memory device, an optical memory device, a magneto-optical memory device, an electronic memory device, etc. Similarly, ROM component 1132 may include any type of read-only memory, such as, for example, a removable memory device, such as a PC-Card or PCMCIA-type device. It should be appreciated that ROM component 1132 and RAM component 1134 may be embodied as a single unit or may be separate units and that ROM component 1132 and/or RAM component 1134 may be provided in the form of a PC-Card or PCMCIA-type device.

Controller 1122 is further connected to front panel 515 of housing 514 and, more particularly, to display device 516 via line 1154 and indicators 518a, 518b via respective lines 1156, 1158. Lines 1116, 1118, 1124, 1126, 1128 electrically and logically connect controller 1122 to first, second, third, fourth and fifth motors 576, 580, 584, 590, 596, respectively. A wired remote control unit ("RCU") 1150 is electrically and logically connected to controller 1122 via line 1152. A wireless RCU 1148 is also provided and communicates via a wireless link 1160 with a receiving/sending unit 1146 connected via line 1144 to a transceiver 1140. The transceiver 1140 is electrically and logically connected to controller 1122 via line 1142. Wireless link 1160 may be, for example, an optical link, such as an infrared link, a radio link or any other form of wireless communication link.

A switch device 1186, which may be, for example, an array of DIP switches, may be connected to controller 1122 via line 1188. Switch device 1186 may be used, for example, to select one of a plurality of languages used in displaying messages and prompts on the display device 516. The messages and prompts may relate to, for example, the operation and/or the status of the electro-mechanical surgical system 510 and/or to the surgical device 11 attached thereto.

According to the example embodiment of the present invention, a first encoder 1106 is provided within the second coupling 526 and is configured to output a signal in response to and in accordance with the rotation of the second drive shaft 530. A second encoder 1108 is also provided within the second coupling 526 and is configured to output a signal in response to and in accordance with the rotation of the first drive shaft 532. The signal output by each of the encoders 1106, 1108 may represent the rotational position of the respective drive shaft 530, 532 as well as the rotational direction thereof. Such encoders 1106, 1108 may be, for example, Hall-effect devices, optical devices, etc. Although the encoders 1106, 1108 are described as being disposed within the second coupling 526, it should be appreciated that the encoders 1106, 1108 may be provided at any location between the motor system and the linear clamping, cutting and stapling device. It should be appreciated that providing the encoders 1106, 1108 within the second coupling 526 or at the distal end of the flexible shaft 520 provides for an accurate determination of the drive shaft rotation. If the encoders 1106, 1108 are disposed at the proximal end of the flexible shaft 520, windup of the first and second rotatable drive shafts 532, 530 may result in measurement error.

Figure 27:
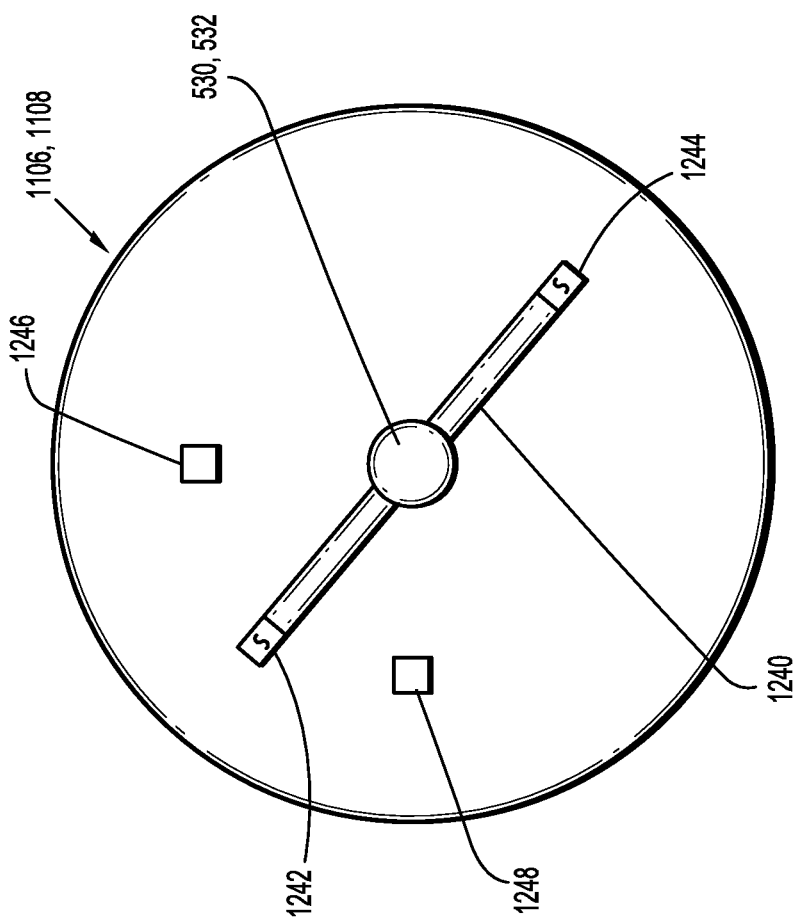
FIG. 27 is a schematic view of an encoder of the flexible shaft illustrated in FIG. 21.

FIG. 27 is a schematic view of an encoder 1106, 1108, which includes a Hall-effect device. Mounted non-rotatably on drive shaft 530, 532 is a magnet 1240 having a north pole 1242 and a south pole 1244. The encoder 1106, 1108 further includes a first sensor 1246 and second sensor 1248, which are disposed approximately 90° apart relative to the longitudinal, or rotational, axis of drive shaft 530, 532. The output of the sensors 1246, 1248 is persistent and changes its state as a function of a change of polarity of the magnetic field in the detection range of the sensor. Thus, based on the output signal from the encoders 1106, 1108, the angular position of the drive shaft 530, 532 may be determined within one-quarter revolution and the direction of rotation of the drive shaft 530, 532 may be determined. The output of each encoder 1106, 1108 is transmitted via a respective line 1110, 1112 of data transfer cable 538 to controller 1122. The controller 1122, by tracking the angular position and rotational direction of the drive shafts 530, 532 based on the output signal from the encoders 1106, 1108, can thereby determine the position and/or state of the components of the linear clamping, cutting and stapling device connected to the electro-mechanical surgical system 510. That is, by counting the revolutions of the drive shaft 530, 532, the controller 1122 can determine the position and/or state of the components of the linear clamping, cutting and stapling device connected to the electro-mechanical surgical system 510.

For instance, the advancement distance of upper jaw 80 relative to lower jaw 50, and of the wedge 270 are functions of, and ascertainable on the basis of, the rotation of the respective drive shaft 530, 532. By ascertaining an absolute position of the jaw 80 and the wedge 270 at a point in time, the relative displacement of the jaw 80 and wedge 270, based on the output signal from the encoders 1106, 1108 and the known pitches of the vertical drive shaft 1132 and lower horizontal shaft 260, may be used to ascertain the absolute position of the jaw 80 and the wedge 270 at all times thereafter. The absolute position of the jaw 80 and the wedge 270 may be fixed and ascertained at the time that the surgical device 11 is first coupled to the flexible shaft 520. Alternatively, the position of the jaw 80 and the wedge 270 relative to, for example, the lower jaw 50 may be determined based on the output signal from the encoders 1106, 1108.

The surgical device 11 may further include, according to one embodiment and as illustrated in FIG. 5, a data connector 1272 adapted by size and configuration to electrically and logically connect to connector 570 of second coupling 526. In the example embodiment, data connector 1272 includes contacts equal in number to the number of leads 572 of connector 570. Contained within the surgical device 11 is a memory unit 1174 electrically and logically connected with the data connector 1272. Memory unit 1174 may be in the form of, for example, an EEPROM, EPROM, etc. and may be contained, for example, within the lower jaw 50 of the surgical device 11.

Figure 28:
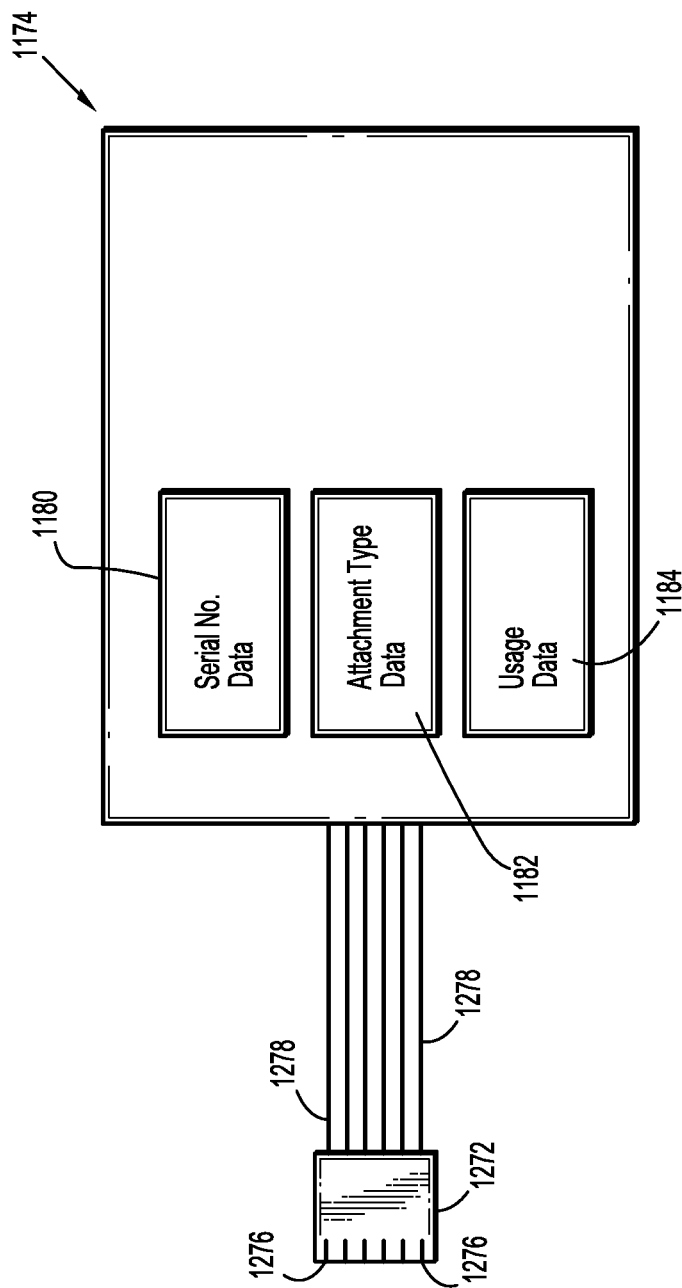
FIG. 28 is a schematic view of a memory device of a linear clamping, cutting and stapling device according to one example embodiment of the present invention.

FIG. 28 schematically illustrates the memory unit 1174. As seen in FIG. 28, data connector 1272 includes contacts 1276, each electrically and logically connected to memory unit 1174 via a respective line 1278. Memory unit 1174 is configured to store, for example, a serial number data 1180, an attachment type identifier (ID) data 1182 and a usage data 1184. Memory unit 1174 may additionally store other data. Both the serial number data 1180 and the ID data 1182 may be configured as read-only data. In the example embodiment, serial number data 1180 is data uniquely identifying the particular linear clamping, cutting and stapling device, whereas the ID data 1182 is data identifying the type of the attachment (when, for instance, other types of attachments may be employed by the device). The usage data 1184 represents usage of the particular attachment, such as, for example, the number of times the upper jaw 80 of the surgical device 11 has been opened and closed, or the number of times that the wedge 270 of the surgical device 11 has been advanced or fired.

It should be appreciated that the attachment attachable to the distal end 524 of the flexible shaft 520, e.g., surgical device 11, may be designed and configured to be used a single time or multiple times. The attachment may also be designed and configured to be used a predetermined number of times. Accordingly, the usage data 1184 may be used to determine whether the surgical device 11 has been used and whether the number of uses has exceeded the maximum number of permitted uses. As more fully described below, an attempt to use the attachment after the maximum number of permitted uses has been reached will generate an ERROR condition.

Referring again to FIG. 26, in accordance with the example embodiment of the present invention, the controller 1122 is configured to read the ID data 1182 from the memory unit 1174 of surgical device 11 when the surgical device 11 is initially connected to the flexible shaft 520. The memory unit 1174 is electrically and logically connected to the controller 1122 via line 1120 of data transfer cable 538. Based on the read ID data 1182, the controller 1122 is configured to read or select from the memory unit 1130, an operating program or algorithm corresponding to the type of surgical instrument or attachment connected to the flexible shaft 520. The memory unit 1130 is configured to store the operating programs or algorithms for each available type of surgical instrument or attachment, the controller 1122 selecting and/or reading the operating program or algorithm from the memory unit 1130 in accordance with the ID data 1182 read from the memory unit 1174 of an attached surgical instrument or attachment. As indicated above, the memory unit 1130 may include a removable ROM component 1132 and/or RAM component 1134. Thus, the operating programs or algorithms stored in the memory unit 1130 may be updated, added, deleted, improved or otherwise revised as necessary. The operating programs or algorithms stored in the memory unit 1130 may be customizable based on, for example, specialized needs of the user. A data entry device, such as, for example, a keyboard, a mouse, a pointing device, a touch screen, etc., may be connected to the memory unit 1130 via, for example, a data connector port, to facilitate the customization of the operating programs or algorithms. Alternatively or additionally, the operating programs or algorithms may be customized and preprogrammed into the memory unit 1130 remotely from the electro-mechanical surgical system 510. It should be appreciated that the serial number data 1180 and/or usage data 1184 may also be used to determine which of a plurality of operating programs or algorithms is read or selected from the memory unit 1130. It should be appreciated that the operating program or algorithm may alternatively be stored in the memory unit 1174 of the surgical device 11 and transferred to the controller 1122 via the data transfer cable 538. Once the appropriate operating program or algorithm is read or selected by, or transmitted to, the controller 1122, the controller 1122 causes the operating program or algorithm to be executed in accordance with operations performed by the user via the wired RCU 1150 (described below) and/or the wireless RCU 1148 (described below). As indicated hereinabove, the controller 1122 is electrically and logically connected with the first, second, third, fourth and fifth motors 576, 580, 584, 590, 596 via respective lines 1116, 1118, 1124, 1126, 1128 and controls such motors 576, 580, 584, 590, 596 in accordance with the read, selected or transmitted operating program or algorithm via the respective lines 1116, 1118, 1124, 1126, 1128.

Figure 29:
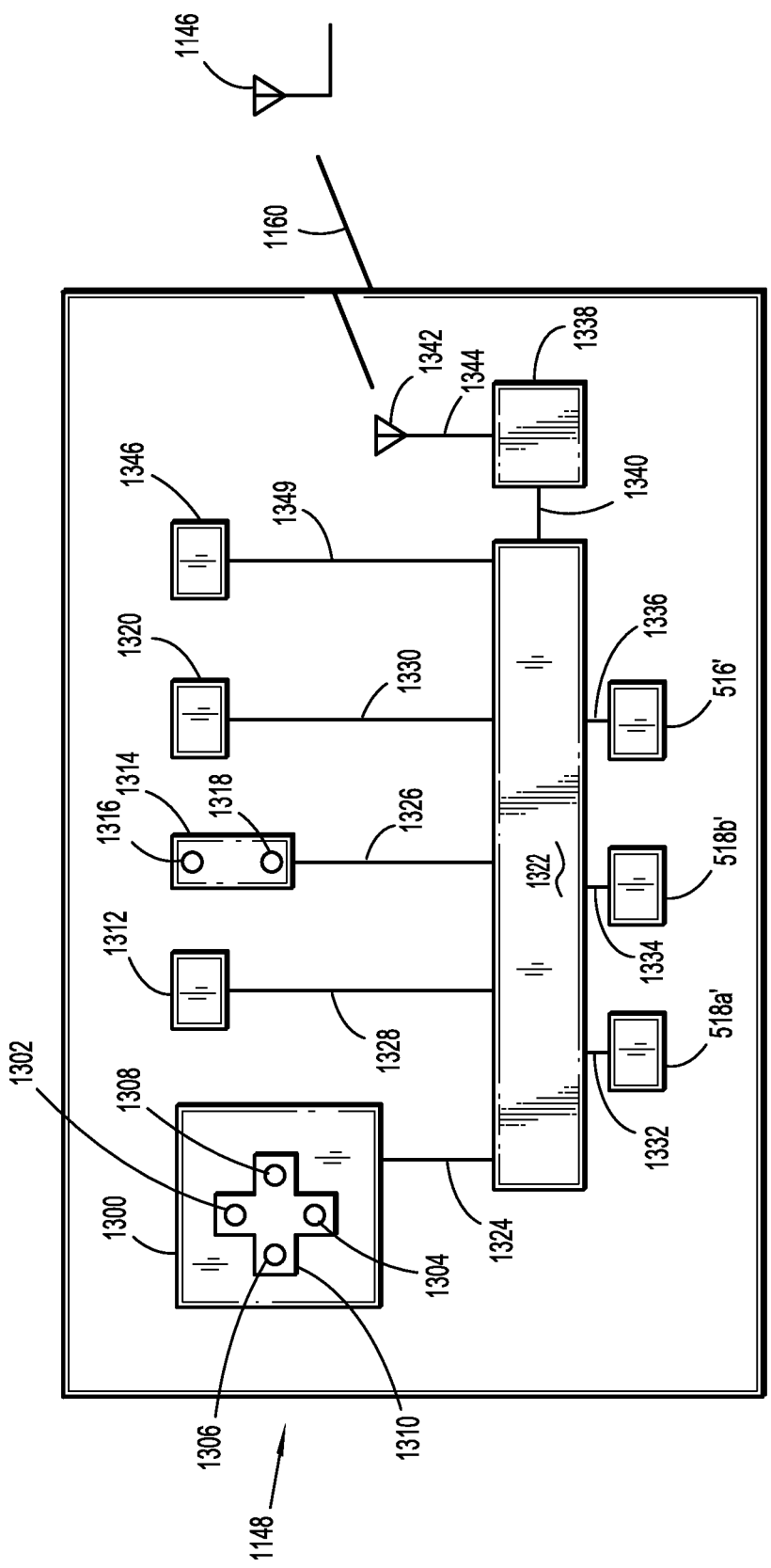
FIG. 29 is a schematic view of a wireless remote control unit of the electro-mechanical surgical device illustrated in FIG. 2.

Referring now to FIG. 29, there is seen a schematic view of wireless RCU 1148. Wireless RCU 1148 includes a steering controller 1300 having a plurality of switches 1302, 1304, 1306, 1308 arranged under a four-way rocker 1310. The operation of switches 1302, 1304, via rocker 1310, controls the operation of first and second steering cables 534, 535 via third motor 584. Similarly, the operation of switches 1306, 1308, via rocker 1310, controls the operation of third and fourth steering cables 536, 537 via fourth motor 592. It should be appreciated that rocker 1310 and switches 1302, 1304, 1306, 1308 are arranged so that the operation of switches 1302, 1304 steers the flexible shaft 520 in the north-south direction and that the operation of switches 1306, 1308 steers the flexible shaft 520 in the east-west direction. Reference herein to north, south, east and west is made to a relative coordinate system. Alternatively, a digital joystick, analog joystick, etc. may be provided in place of rocker 1310 and switches 1302, 1304, 1306, 1308. Potentiometers or any other type of actuator may also be used in place of switches 1302, 1304, 1306, 1308.

Wireless RCU 1148 further includes a steering engage/disengage switch 1312, the operation of which controls the operation of fifth motor 596 to selectively engage and disengage the steering mechanism. Wireless RCU 1148 also includes a two-way rocker 1314 having first and second switches 1316, 1318 operable thereby. The operation of these switches 1316, 1318 controls certain functions of the electro-mechanical surgical system 510 and any surgical instrument or attachment, such as the surgical device 11, attached to the flexible shaft 520 in accordance with the operating program or algorithm corresponding to the attached device 11. For example, operation of the two-way rocker 1314 may control the opening and closing of the upper and lower jaws of the surgical device 11. Wireless RCU 1148 is provided with yet another switch 1320, the operation of which may further control the operation of the electro-mechanical surgical system 510 and the device attached to the flexible shaft 520 in accordance with the operating program or algorithm corresponding to the attached device. For example, operation of the switch 1320 may initiate the advancement, or firing sequence, of the wedge 270 of the surgical device 11.

Wireless RCU 1148 includes a controller 1322, which is electrically and logically connected with the switches 1302, 1304, 1306, 1308 via line 1324, with the switches 1316, 1318 via line 1326, with switch 1312 via line 1328 and with switch 1320 via line 1330. Wireless RCU 1148 may include indicators 518a', 518b', corresponding to the indicators 518a, 518b of front panel 515, and a display device 516', corresponding to the display device 516 of the front panel 515. If provided, the indicators 518a', 518b' are electrically and logically connected to controller 1322 via respective lines 1332, 1334, and the display device 516' is electrically and logically connected to controller 1322 via line 1336. Controller 1322 is electrically and logically connected to a transceiver 1338 via line 1340, and transceiver 1338 is electrically and logically connected to a receiver/transmitter 1342 via line 1344. A power supply, not shown, for example, a battery, may be provided in wireless RCU 1148 to power the same. Thus, the wireless RCU 1148 may be used to control the operation of the electro-mechanical surgical system 510 and the device 11 attached to the flexible shaft 520 via wireless link 1160.

Wireless RCU 1148 may include a switch 1346 connected to controller 1322 via line 1348. Operation of switch 1346 transmits a data signal to the transmitter/receiver 1146 via wireless link 1160. The data signal includes identification data uniquely identifying the wireless RCU 1148. This identification data is used by the controller 1122 to prevent unauthorized operation of the electro-mechanical surgical system 510 and to prevent interference with the operation of the electro-mechanical surgical system 510 by another wireless RCU. Each subsequent communication between the wireless RCU 1148 and the electro-mechanical device surgical 510 may include the identification data. Thus, the controller 1122 can discriminate between wireless RCUs and thereby allow only a single, identifiable wireless RCU 1148 to control the operation of the electro-mechanical surgical system 510 and the device 11 attached to the flexible shaft 520.

Based on the positions of the components of the device attached to the flexible shaft 520, as determined in accordance with the output signals from the encoders 1106, 1108, the controller 1122 may selectively enable or disable the functions of the electro-mechanical surgical system 510 as defined by the operating program or algorithm corresponding to the attached device. For example, for the surgical device 11, the firing function controlled by the operation of the switch 1320 is disabled unless the space or gap between lower jaw 50 and upper jaw 80 is determined to be within an acceptable range. The space or gap between lower jaw 50 and upper jaw 80 is determined based on the output signal from the encoders 1106, 1108, as more fully described hereinabove. It should be appreciated that, in the example embodiment, the switch 1320 itself remains operable but the controller 1122 does not effect the corresponding function unless the space or gap is determined to be within the acceptable range.

Figure 30:
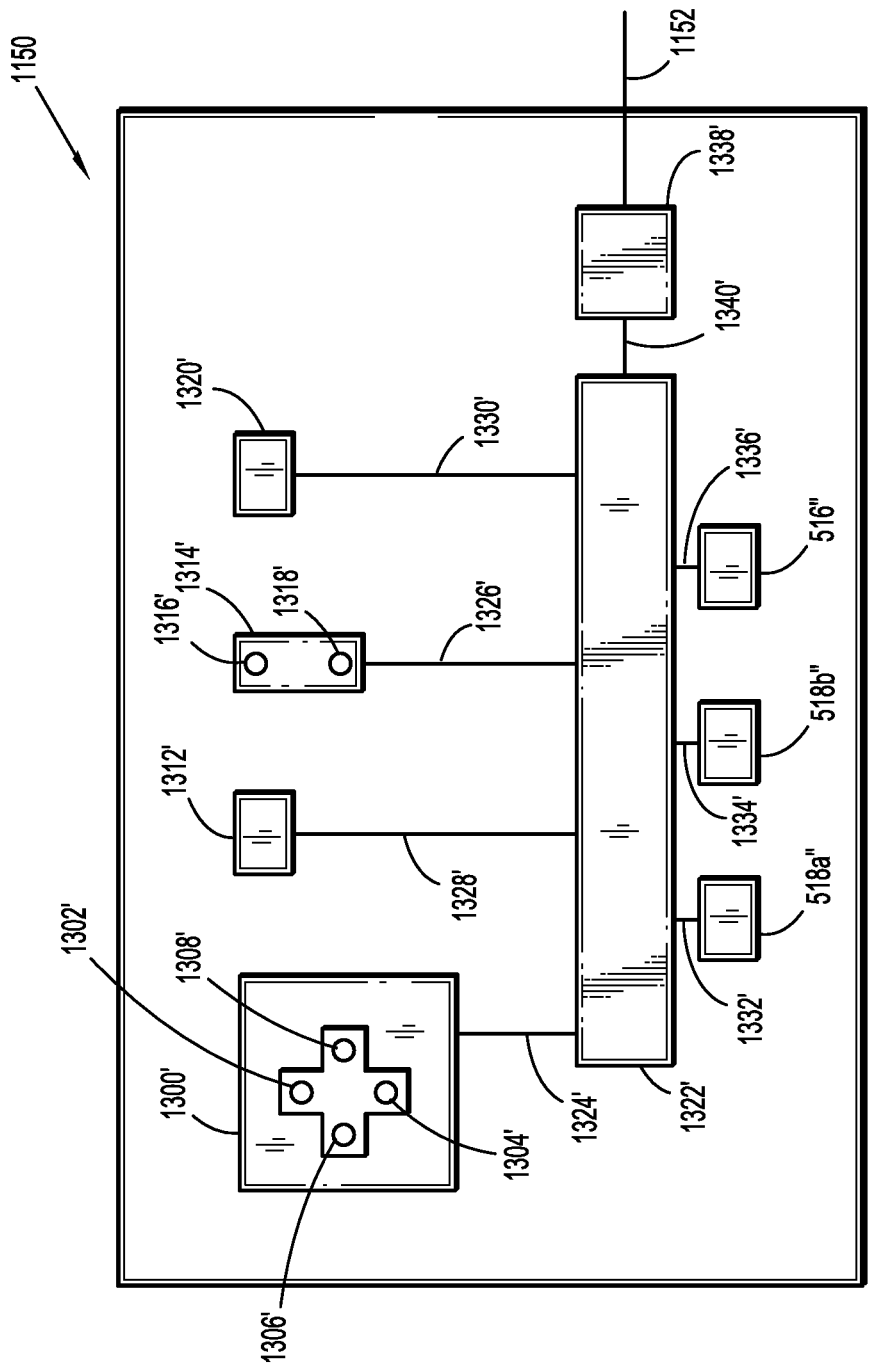
FIG. 30 is a schematic view of a wired remote control unit of the electro-mechanical surgical device illustrated in FIG. 2.

Referring now to FIG. 30, there is seen a schematic view of a wired RCU 1150. In the example embodiment, wired RCU 1150 includes substantially the same control elements as the wireless RCU 1148 and further description of such elements is omitted. Like elements are noted in FIG. 30 with an accompanying prime. It should be appreciated that the functions of the electro-mechanical surgical system 510 and the device attached to the flexible shaft 520 (e.g., the surgical device 11) may be controlled by the wired RCU 1150 and/or by the wireless RCU 1148. In the event of a battery failure, for example, in the wireless RCU 1148, the wired RCU 1150 may be used to control the functions of the electro-mechanical surgical system 510 and the device attached to the flexible shaft 520.

As described hereinabove, the front panel 515 of housing 514 includes display device 516 and indicators 518a, 518b. The display device 516 may include an alpha-numeric display device, such as an LCD display device. Display device 516 may also include an audio output device, such as a speaker, a buzzer, etc. The display device 516 is operated and controlled by controller 1122 in accordance with the operating program or algorithm corresponding to the device attached to the flexible shaft 520 (e.g., the surgical device 11). If no surgical instrument or attachment is so attached, a default operating program or algorithm may be read or selected by, or transmitted to, controller 1122 to thereby control the operation of the display device 516 as well as the other aspects and functions of the electro-mechanical surgical system 510. If surgical device 11 is attached to flexible shaft 520, display device 516 may display, for example, data indicative of the gap between lower jaw 50 and upper jaw 80 as determined in accordance with the output signal of encoders 1106, 1108, as more fully described hereinabove.

Similarly, the indicators 518a, 518b are operated and controlled by controller 1122 in accordance with the operating program or algorithm corresponding to the device 11, attached to the flexible shaft 520 (e.g., the surgical device 11). Indicator 518a and/or indicator 518b may include an audio output device, such as a speaker, a buzzer, etc., and/or a visual indicator device, such as an LED, a lamp, a light, etc. If the surgical device 11 is attached to the flexible shaft 520, indicator 518a may indicate, for example, that the electro-mechanical surgical system 510 is in a power ON state, and indicator 518b may, for example, indicate whether the gap between lower jaw 50 and upper jaw 80 is determined to be within the acceptable range as more fully described hereinabove. It should be appreciated that although only two indicators 518a, 518b are described, any number of additional indicators may be provided as necessary. Additionally, it should be appreciated that although a single display device 516 is described, any number of additional display devices may be provided as necessary.

The display device 516' and indicators 518a', 518b' of wired RCU 1150 and the display device 516" and indicators 518a", 518b" of wireless RCU 1148 are similarly operated and controlled by respective controller 1322, 1322' in accordance with the operating program or algorithm of the device attached to the flexible shaft 520.

As previously mentioned, the surgical device 11 may be employed to clamp, cut and staple a section of tissue. The operation of the surgical device 11 will now be described in connection with the removal of a cancerous or anomalous section of tissue in a patient's bowel, which is, of course, merely one type of tissue and one type of surgery that may be performed using the surgical device 11. Generally, in operation, after cancerous or anomalous tissue has been located in the gastrointestinal tract, the patient's abdomen is initially opened to expose the bowel. Utilizing the remote actuation provided by the electro-mechanical surgical system 510, the upper and lower jaws 50, 80 of the surgical device 11 are driven into the open position. The tube of the bowel is then placed on a side adjacent to the cancerous tissue between the spread jaws. Again, by remote actuation, the second driver is caused to engage in reverse, and the upper jaw closes onto the bowel and the lower jaw. Once the bowel has been sufficiently clamped, the first driver is engaged, which causes the wedge to advance simultaneously from the distal end of the attachment to the proximal end thereof, thereby cutting and stapling the bowel. This step is then repeated on the other side of the cancerous tissue, thereby removing the section of bowel containing the cancerous tissue, which is stapled on either end to prevent spilling of bowel material into the open abdomen.

More specifically, according to the example embodiment of the present invention, the surgical device 11 is coupled to the attachment socket or coupling 26 of the electro-mechanical driver component 510 such that the upper drive socket 180 engages the corresponding flexible drive shaft 530 of the electro-mechanical driver component 510 and the second drive socket 310 engages the corresponding flexible drive shaft 532 of the electro-mechanical driver component 510. Thus, rotation of the upper horizontal shaft 151 is effected by rotation of the upper drive socket 180 which is effected by rotation of the corresponding flexible drive shaft 530 of the electro-mechanical driver component 510. Clockwise or counter-clockwise rotation is achieved depending on the direction of the motor 580. Similarly, rotation of the lower horizontal shaft 260 is effected by rotation of the second drive socket 310 which is effected by rotation of the corresponding flexible drive shaft 532 of the electro-mechanical driver component 510. Again, clockwise or counter-clockwise rotation is achieved depending on the direction of the motor 576.

In order to clamp the exposed ends of the bowel, the upper motor 580 corresponding to the upper flexible drive shaft 530 is activated, which engages the upper drive socket 180 at the proximal end 170 of the upper horizontal shaft 151, thereby causing the upper horizontal shaft 151 to turn in a first (e.g., clockwise) rotation. When the surgical device 11 is in an initial closed state as illustrated in FIG. 5, this first rotation of the upper horizontal shaft 151 causes the outer threads 152 of the upper horizontal shaft 151 to engage the outer threads 132 of the vertical shafts 130, thereby causing the vertical shafts 130 to turn in a similar first (e.g., clockwise) rotation. This rotation of the vertical shafts 130 causes the outer threads 132 of the vertical shafts 130 to channel within the inner threads 92 of the vertical bores 90, thereby causing the upper jaw 80 to rise in a continuous fashion (in the embodiment illustrated, in a parallel alignment with the fixed lower jaw 50) and begin separating from the lower jaw 50. Continuous operation of the motor in this manner eventually places the surgical device 11 in an open state, providing a space between the upper jaw 80 and the lower jaw 50, as illustrated in FIG. 6.

Once the surgical device 11 is in this open state, the tray 220 of staples 230 may be accessible, and may be inspected to determine whether the staples 230 are ready for the procedure and/or replace the tray 220 with a more suitable tray 220. In addition, the status of the surgical device 11 may be determined by the control system 1122 as described hereinabove. Once the tray 220 is determined to be ready and in place, a section of the colon is placed between the upper jaw 80 and lower jaw 50. Thereafter, the upper motor 580 is reversed to effect a second (e.g., counter-clockwise) rotation of the upper horizontal shaft 151, which in turn effects counter-clockwise rotation of the vertical shafts 130, which in turn effects a lowering of the upper jaw 80. Continuous operation of the upper motor 580 in this manner eventually returns the linear clamping and stapling device to a closed state, in which the distal end of the bowel is clamped between the upper jaw 80 and the lower jaw 40.

The clamping of the distal end of the bowel is determined in accordance with the output sensors 1246 and 1248 or output electrodes 182, 184 as described above. Circuit components in the electro-mechanical surgical system 510 may provide an alert to signal that it is safe and/or appropriate to begin the cutting and stapling procedure. To begin the stapling and cutting procedure, the lower motor 576 of the electro-mechanical driver component corresponding to the lower flexible drive shaft 532 is activated, which engages the lower drive socket 310 at the proximal end 300 of the lower horizontal shaft 260, thereby causing the lower horizontal shaft 260 to turn in a first (e.g., counter-clockwise) rotation. When the stapling and cutting mechanism is in an initial loaded state, the wedge 270 and the blade 51 associated therewith are in the channel 250 at a position farthest from the proximal end 300 of the lower horizontal shaft 260 (i.e., at the distal end). The counter-clockwise rotation of the lower horizontal shaft 260 causes the outer threads 262 of the lower horizontal shaft 260 to engage the inner threads 292 of the horizontal threaded bore 290 of the wedge 270, thereby causing the wedge 270 to travel through the channel 250 in a proximal direction toward the proximal end 300 of the lower horizontal shaft 260. Continuous operation of the lower motor 576 in this manner will move the wedge 270 fully through the channel 250. As the wedge 270 moves through proximally the channel, the blade 51 mounted to the top of the wedge cuts through the bowel, thereby transecting it. Simultaneously, the sloped top face 280 of the wedge 270 contacts the butts 232 of the staples 230, thereby pushing the prongs 234 of the staples 230 through the tissue of the clamped distal end of bowel and against the staple guides 240, which bends and closes the staples 230. When the wedge 270 is moved proximally fully through the channel 250, all of the staples 230 are pushed through the tray 220 and closed, thereby stapling closed the distal end of the bowel on both sides of the cut.

Thereafter, the upper motor 580 is again activated to effect a clockwise rotation of the upper horizontal shaft 151, which in turn effects a clockwise rotation of the vertical shafts 130, which in turn effects a raising of the upper jaw 80. Continuous operation of the upper motor 580 in this manner eventually returns the surgical device 11 into the open state. Thereafter, the empty tray 220 is replaced with a full tray 220 and the same clamping, cutting and stapling procedure is performed on the proximal end of the bowel. It should be understood that prior to the secure clamping, cutting and stapling procedure, the blade 51 and the wedge 270 may be returned to the distal position by operation of the lower motor 576. In order to accomplish this, the lower motor 576 is reversed to effect a clockwise rotation of the lower horizontal shaft 260, which in turn moves the wedge 270 away from the proximal end 300 of the lower horizontal shaft 260. Continuous operation of the lower motor 576 in this manner eventually returns the wedge 270 to its initial position at the distal end of the mechanism. Once the proximal end of the bowel is also clamped, cut and stapled, the attachment (i.e., the surgical device 11) may be separated from the electro-mechanical driver component and discard the attachment.

As previously mentioned, FIGS. 31 to 33 illustrate an alternative example embodiment, wherein the surgical device 11 includes a blade 651 rotatably coupled to a wedge 670 so as to rotate between a first and a second position. The steps performed in order to operate this alternative example embodiment of the surgical device 11 are substantially similar to the steps described above as performed in order to operate the example embodiment of the surgical device 11 illustrated in FIGS. 5 and 6. The operation of those additional features of the surgical device 11 of the alternative example embodiment illustrated in FIGS. 31 to 33 will now be described. Referring to FIG. 31, and as previously discussed, the wedge 270 is illustrated as being located at the distal end of the lower jaw 50 after the clamping operation has been performed but before the cutting and stapling operation has begun. The blade 651 is rotatably mounted to the wedge 270 by pivot member 652. The cutting edge 651*a* of the blade 651 is initially disposed in a retracted or down position, e.g., facing lower horizontal shaft 260. The tail region 654 of the blade 651 is disposed above the wedge 270, so that the actuating pin receiving face 653 initially faces the proximal end 170 of the surgical device 11 and is adjacent to fixed actuating pin 655 of lower jaw 50.

FIG. 32 illustrates the surgical device 11 in which the cutting and stapling operation has begun, e.g., by rotating horizontal shaft 260 so as to begin moving the wedge 270 from the distal end of the lower jaw 50 toward the proximal end of the lower jaw 50. As illustrated in FIG. 32, the actuating pin receiving face 653 located at the tail region 654 of blade 651 engages fixed actuating pin 655, causing the blade 651 to rotate relative to the wedge 270 around pivot member 652. By rotating relative to the wedge 270 around pivot member 652, the cutting edge 651*a* of the blade 651 is displaced from its initial position facing the lower horizontal shaft 260 and begins to swing upwardly.

FIG. 33 illustrates the surgical device 11 in which the cutting and stapling operation has continued further, e.g., by further rotating horizontal shaft 260 so as to continue to move the wedge 270 from the distal end of the lower jaw 50 toward the proximal end of the lower jaw 50. As illustrated in FIG. 33, the wedge 270 has moved proximally far enough toward the proximal end of the lower jaw 50 so as to cause actuating pin receiving face 653 at the tail region 654 of blade 651 to complete its engagement with fixed actuating pin 655. At this point, the blade 651 is rotated relative to the wedge 270 around pivot member 652 such that the cutting edge 651*a* of the blade 651 faces the proximal end of the lower jaw 50.

As previously mentioned, one problem of conventional cutting and stapling devices is that the opposing jaws of the mechanism tend to open, or be urged apart, during operation. This follows because the force exerted by the sloped top face 280 of wedge 270 has an upward component when sloped face 280 contacts the butt 232 of the staples 230 in the staple tray 220 and urges the prongs 234 of the staples 230 into the opposing staple guides 240. As prongs 234 contact guides 240, the force of the contact tends to separate, or urge apart, the upper and lower jaws until the prongs 234 of the staples are bent by guides 240 into a closed position. If the upper and lower jaws separate by a sufficient distance, the prongs 234 will not be sufficiently bent by guides 240 into the closed position, and the inadequately stapled end of the tissue may permit its contents to spill into the open abdomen of the patient, increasing the likelihood of infection and other complications.

In accordance with the example embodiment of the present invention, movement of the cutting and stapling element, e.g., the wedge 270 and blade 51, from the distal end of the surgical device 11 to the proximal end during the cutting and stapling operation may reduce the tendency of the upper and lower jaws to separate, or to be urged apart, during the cutting and stapling operation. Specifically, by moving the cutting and stapling element, e.g., the wedge 270 and the blade 51, from the distal end of the surgical device 11 to the proximal end during the cutting and stapling operation, there may be a resulting reduction in the distance between the upper and lower jaws at its distal end. For instance, in linear clamping, cutting and stapling devices in which a wedge/blade is moved from the proximal end to the distal end during the stapling and cutting operation, the first staple encountered by the wedge is the staple that is located closest to the proximal end. When the wedge contacts the butt of this first staple, the wedge forces the prongs of the staple into contact with the opposing staple guide in the upper jaw. Until the prongs have been bent and closed, this contact between the prongs of the staple and the opposing staple guide causes the distance between the upper and lower jaws, at the proximal end thereof, to increase by a small amount. However, because the upper and lower jaws are mechanically, e.g., pivotably, connected at the proximal end but are free at the distal end, the small increase in the distance between the upper and lower jaws at the proximal end translates into a relatively large increase in the distance between the upper and lower jaws at the distal end. Simultaneously, while the blade is cutting the tissue clamped between the upper and lower jaws, the distal movement of the blade also tends to push the tissue clamped between the upper and lower jaws toward the distal end of the jaws. Because the jaws have been forced apart at their distal end, a greater amount (i.e., thickness) of tissue may be accommodated at the distal end of the jaws, and the pushing action of the blade against the tissue tends to push, the greater amount of tissue into the space at the distal end of the jaws. Once the additional tissue is accommodated between the distal ends of the upper and lower jaws, the tissue further acts to force the distal ends of the jaws apart. Thus, when the cutting and stapling element has traveled to the distal end of the jaws, the distance between the jaws at the distal end may be undesirably large, and effective stapling of the tissue between the distal ends of the jaws may be less than optimal.

By contrast, in accordance with the example embodiment of the present invention, the first staple 230 encountered by the wedge 270 is the staple which is located closest to the distal end of the lower jaw 50. When the wedge 270 contacts the butt 232 of this first staple, the wedge 270 forces the prongs 234 of the staple 230 into contact with the opposing staple guide 240 in the upper jaw 80. This contact between the prongs 234 of the staple 230 and the opposing staple guide 240 may cause the distance between the upper jaw 80 and the lower jaw 50 at the distal ends thereof, to increase by a small amount, because the upper jaw 80 and lower jaw 50 are free at their distal end. However, because the upper jaw 80 and lower jaw 50 are mechanically connected at their proximal ends, the small increase in the distance between the upper jaw 80 and lower jaw 50 at their distal end does not translate into a corresponding large increase in the distance between the upper jaw 80 and lower jaw 50 at their proximal ends. Furthermore, in the example embodiment of the present invention, while the blade 51 is cutting the tissue clamped between the upper jaw 50 and lower jaw 80, the horizontal movement of the blade 51 tends to push the tissue clamped between the upper jaw 80 and lower jaw 50 towards the proximal end of the jaws. However, because the upper jaw 80 and lower jaw 50 have not been forced apart at their proximal ends, a greater amount (i.e., thickness) of tissue may not be accommodated at the proximal ends of the jaws, and the cutting force of the blade 51 against the tissue may not tend to push a greater amount of tissue into the space at the proximal end of the jaws. Thus, since no additional tissue may be accommodated between the proximal ends of the upper jaw 80 and the lower jaw 50, the tissue may not further act to force the proximal ends of the jaws apart. Thus, by the time the cutting and stapling element, e.g., the blade 51 and the wedge 270, has traveled to the proximal end of the lower jaw 50, the distance between the lower jaw 50 and the upper jaw 80 at the proximal end may remain substantially unchanged, thereby insuring optimal effectiveness for stapling of the tissue between the proximal ends of the lower and upper jaws 50, 80. Also, when the wedge 270 eventually contacts the staples 230 at the proximal end of the jaws 50, 80, the distance between the upper and lower jaws 50, 80, at their proximal end may increase by a small amount. However, since the tissue located at the distal end has already been cut and stapled, any larger distance between the upper jaw 80 and the lower jaw 50 at the distal end at this time is irrelevant. Thus, the present invention insures optimal effectiveness of stapling by reducing the tendency of the upper and lower jaws to separate during operation.

The example embodiment of the present invention may also reduce the torque which is required to move the wedge 270 and may therefore reduce the stress which is experienced by various components of the surgical device. For instance, in linear clamping, cutting and stapling devices, which move a wedge/blade from the proximal end to the distal end, the torque that is required to move the wedge/blade increases as the wedge/blade moves from the proximal end to the distal end, because the distance between the wedge/blade and the proximal end of the device (the point at which the rotatable drive shaft is coupled to the device) increases. In addition, the torque that is required to move the wedge/blade also increases as the wedge/blade moves from the proximal end to the distal end, because of the additional tissue accommodated at the distal end of the device. As discussed above, while the blade is cutting the tissue clamped between the upper and lower jaws, the distal movement of the blade also tends to push the tissue clamped between the upper and lower jaws towards the distal end of the jaws. In order to cut through the greater amount (i.e., thickness) of tissue accommodated at the distal end of the jaws, a greater amount of torque is required to be imparted by the horizontal drive shaft to the wedge/blade. Thus, when the cutting and stapling element has traveled to the distal end of the jaws, the torque has increased, thereby causing stress in the wedge/blade, and drive mechanisms of the device.

In contrast, in accordance with the example embodiment of the present invention, there may be a reduction in the torque that is required to move the wedge 270 during the cutting and stapling operation, thereby reducing the stress that is experienced by various components of the surgical device 11. For instance, in surgical device 11, which moves the wedge 270 and blade 51 from the distal end to the proximal end of the lower jaw 50, the torque that is required to move the wedge 270 and the blade 51 decreases as the wedge 270 and the blade 51 move from the distal end to the proximal end of lower jaw 50 because the distance between the wedge/blade and the proximal end of the device (the point at which the rotatable drive shaft is coupled to the device) decreases. In addition, the torque that is required to move the wedge/blade also decreases as the wedge/blade moves from the distal end of lower jaw 50 to the distal end, because there is no additional tissue accommodated at the proximal end of the jaws 50 and 80. Unlike conventional linear clamping, cutting and stapling devices, while the blade 51 of the surgical device 11 is cutting the tissue clamped between the upper jaw 80 and the lower jaw 50, the proximal movement of the blade 51 does not tend to push the tissue clamped between the upper jaw 80 and the lower jaw 50 toward the proximal end of the jaws. Thus, since the blade 51 is not required to cut through a greater amount (i.e., thickness) of tissue accommodated at the proximal end of the jaws, a greater amount of torque is not required to be imparted by the lower horizontal shaft 260 to the wedge 270 and the blade 51 in order to cut the tissue. When the wedge 270 and the blade 51 have traveled to the proximal end of the lower jaw 50, the torque has decreased, thereby reducing the stress in the wedge 270, blade 51, first driver 261, etc.

The example embodiment of the present invention may also reduce the length of a linear clamping, cutting and stapling device, thereby improving the device's ability to be employed in small spaces. Because a linear clamping, cutting and stapling device may be intended to be employed corporeally, e.g., inside the body of a patient, the device must be small enough to be maneuvered inside the body of the patient. In conventional linear clamping, cutting and stapling devices, which move a wedge/blade from the proximal end to the distal end, the space that is required in order to house the wedge/blade at the proximal end of the device increases the overall length of the device. This increase in the length of the device makes the device more difficult to maneuver inside the patient's body.

In contrast, in accordance with the example embodiment of the present invention, the surgical device 11 initially houses wedge 270 and blade 51 at the distal end of lower jaw 50, which is unencumbered by the memory unit 1174, vertical drive shafts 130, and various other components that are located at the proximal end of surgical device 11. Thus, by initially disposing the wedge 270 and the blade 51 at the distal end of lower jaw 50, and by moving the wedge 270 and the blade 51 from the distal end of lower jaw 50 to the proximal end, the overall length of surgical device 11 relative to conventional linear clamping, cutting and stapling devices may be reduced. This decrease in overall length makes the surgical device 11 easier to maneuver inside the patient's body, as compared to conventional linear clamping, cutting and stapling devices.

By decreasing the required overall length of surgical device 11 relative to conventional linear clamping, cutting and stapling devices, according to an example embodiment, the surgical device 11 may also provide a corresponding increase (approximately 30%) in the length of its stroke, e.g., the distance which the wedge 270 and the blade 51 may travel during the cutting and stapling operation, as compared to conventional linear clamping, cutting and stapling devices. For instance, since the overall length of surgical device 11 may be reduced (relative to the overall length of conventional linear clamping, cutting and stapling devices) due to the space saved by initially positioning the wedge 270 and the blade 51 at the distal end, the saved space may also increase the stroke length of the surgical device 11. Thus, the surgical device 11 may be configured, according to one example embodiment, to clamp, cut and staple larger sections of tissue than conventional linear clamping, cutting and stapling devices.

The example embodiment illustrated in FIGS. 31 to 33 may also improve the safety of the surgical device 11 in that the cutting edge 651 a of the blade 651 is retracted, e.g., not exposed, when the wedge 270 is in an initial position at the distal end of lower jaw 50. Specifically, according to this example embodiment, during the stage of the operation when the section of tissue to be clamped, cut and stapled is placed and clamped between upper jaw 80 and lower jaw 50 of the surgical device 11, the cutting edge 651a of the blade 651 is retracted. By retracting the cutting edge 651a of the blade 651 during this positioning and clamping stage of the operation, the likelihood that the section of tissue will be inadvertently cut before the section of tissue is adequately clamped may be decreased. Furthermore, accidental cutting by blade 651 of, for example, an operator or other equipment, may be reduced by the arrangement of the retracted blade 651. According to the example embodiment, only after the section of tissue has been clamped (and it has been determined that it is appropriate to start the cutting and clamping stage of the operation) is the wedge 270 moved toward the proximal end of the lower jaw 50, thereby causing the cutting edge 651 a of the blade 651 to be disposed in a cutting position, e.g., facing the proximal end of lower jaw 50.

Thus, the several aforementioned objects and advantages of the present invention are most effectively attained. Those skilled in the art will appreciate that numerous modifications of the exemplary embodiment described hereinabove may be made without departing from the spirit and scope of the invention. Although a single exemplary embodiment of the present invention has been described and disclosed in detail herein, it should be understood that this invention is in no sense limited thereby.

What is claimed is:

1. A surgical device, comprising:
   a first jaw defining a longitudinal axis;
   a second jaw mechanically coupled in opposed relation to the first jaw;
   a cutting element disposed within and rotatable relative to the second jaw;
   a first sensor electrode disposed on the first jaw and configured to electrically communicate with a first contact pad; and
   a second sensor electrode disposed on the second jaw and configured to electrically communicate with a second contact pad, the second contact pad arranged to electrically communicate with the first contact pad.

2. The surgical device according to claim 1, wherein when the first jaw and the second jaw are approximated to a closed configuration, the first sensor electrode contacts the second sensor electrode to complete a sensor circuit.

3. The surgical device according to claim 2, wherein the sensor circuit provides an indication that a cutting and fastening of tissue, disposed between the first jaw and the second jaw, is permitted.

4. The surgical device according to claim 3, wherein the indication is an alert provided to an operator to initiate the cutting and fastening of tissue.

5. The surgical device according to claim 4, wherein the alert is at least one of an audible indication and a visual indication.

6. The surgical device according to claim 2, wherein the contacting of the first sensor electrode and the second sensor electrode automatically activates a cutting and fastening mechanism for cutting and fastening of tissue.

7. The surgical device according to claim 1, wherein the first sensor electrode is in electrical communication with a first contact node, and the second sensor electrode is in electrical communication with a second contact node, the second contact node arranged to electrically communicate with the first contact node.

8. The surgical device according to claim 7, wherein the first sensor electrode and the second sensor electrode are in electrical communication with an electromechanical driver device, via the respective contact nodes, to form a sensor circuit.

9. The surgical device according to claim 1, further comprising:
   a first rotatable shaft coupled to the first jaw, wherein a rotation of the first rotatable shaft causes the first jaw to travel linearly in a direction perpendicular to the longitudinal axis; and
   a second rotatable shaft arranged in parallel to the longitudinal axis of the first jaw, wherein a rotation of the second rotatable shaft causes a cutting and fastening mechanism to travel linearly in a direction parallel to the longitudinal axes of the first and second jaws.

10. The surgical device according to claim 9, further comprising:
    an upper horizontal shaft coupled to a proximal end of the first jaw; and
    a lower horizontal shaft extending through the second jaw, the upper horizontal shaft and the lower horizontal shaft configured to be parallel to each other at a fixed distance.

11. An electro-mechanical surgical system, comprising:
    an elongated shaft;
    a first axially rotatable drive shaft disposed within the elongated shaft;
    a surgical device configured to detachably couple to a distal end of the elongated shaft, wherein the surgical device includes:
      a first jaw defining a longitudinal axis;
      a second jaw mechanically coupled in opposed relation to the first jaw;
      a cutting element disposed within and rotatable relative to the second jaw;
      a first sensor electrode disposed on the first jaw and configured to electrically communicate with a first contact pad; and
      a second sensor electrode disposed on the second jaw and configured to electrically communicate with a second contact pad, the second contact pad arranged to electrically communicate with the first contact pad.

12. The electro-mechanical surgical system according to claim 11, wherein when the first jaw and the second jaw are approximated to a closed configuration, the first sensor electrode contacts the second sensor electrode to complete a sensor circuit.

13. The electro-mechanical surgical system according to claim 12, wherein the sensor circuit provides an indication that a cutting and fastening of tissue, disposed between the first jaw and the second jaw, is permitted.

14. The electro-mechanical surgical system according to claim 13, wherein the indication is an alert provided to an operator to initiate the cutting and fastening of tissue.

15. The electro-mechanical surgical system according to claim 14, wherein the alert is at least one of an audible indication and a visual indication.

16. The electro-mechanical surgical system according to claim 12, wherein the contacting of the first sensor electrode and the second sensor electrode automatically activates a cutting and fastening mechanism for cutting and fastening of tissue.

17. The electro-mechanical surgical system according to claim 11, wherein the first sensor electrode is in electrical communication with a first contact node, and the second sensor electrode is in electrical communication with a second contact node, the second contact node arranged to electrically communicate with the first contact node.

18. The electro-mechanical surgical system according to claim 17, wherein the first sensor electrode and the second sensor electrode are in electrical communication with an electromechanical driver device, via the respective contact nodes, to form a sensor circuit.

19. The electro-mechanical surgical system according to claim 11, further comprising:
   a first rotatable shaft coupled to the first jaw, wherein a rotation of the first rotatable shaft causes the first jaw to travel linearly in a direction perpendicular to the longitudinal axis; and
   a second rotatable shaft arranged in parallel to the longitudinal axis of the first jaw, wherein a rotation of the second rotatable shaft causes a cutting and fastening mechanism to travel linearly in a direction parallel to the longitudinal axes of the first and second jaws.

20. The electro-mechanical surgical system according to claim 19, further comprising:
   an upper horizontal shaft coupled to a proximal end of the first jaw; and
   a lower horizontal shaft extending through the second jaw, the upper horizontal shaft and the lower horizontal shaft configured to be parallel to each other at a fixed distance.

* * * * *